United States Patent
Oh et al.

(10) Patent No.: US 11,890,245 B2
(45) Date of Patent: Feb. 6, 2024

(54) SKIN CARE DEVICE

(71) Applicants: LG HOUSEHOLD & HEALTH CARE LTD., Seoul (KR); AMOSENSE CO., LTD., Cheonan-si (KR)

(72) Inventors: Sung Taek Oh, Seoul (KR); Sang Dong Jeong, Cheonan-si (KR); Jin Pyo Park, Cheonan-si (KR); Hyung Kyu Kim, Seoul (KR); Jung Yong Lee, Seoul (KR); Kyung Won Kim, Seoul (KR)

(73) Assignees: LG HOUSEHOLD & HEALTH CARE LTD., Seoul (KR); AMOSENSE CO., LTD., Cheonan-si (KR)

( * ) Notice: Subject to any disclaimer, the term of this patent is extended or adjusted under 35 U.S.C. 154(b) by 645 days.

(21) Appl. No.: 17/087,677

(22) Filed: Nov. 3, 2020

(65) Prior Publication Data
US 2021/0145686 A1    May 20, 2021

(30) Foreign Application Priority Data
Nov. 14, 2019 (KR) .................. 10-2019-0145605

(51) Int. Cl.
*A61H 1/00* (2006.01)
*A61N 1/04* (2006.01)
(Continued)

(52) U.S. Cl.
CPC .............. *A61H 1/00* (2013.01); *A61H 23/02* (2013.01); *A61N 1/0408* (2013.01);
(Continued)

(58) Field of Classification Search
CPC .............. A61H 1/00; A61H 2201/10; A61H 2201/105; A61H 23/00–006;
(Continued)

(56) References Cited

U.S. PATENT DOCUMENTS

| 10,376,693 B2 | 8/2019 | Yamazaki |
| 2005/0054957 A1* | 3/2005 | Yamazaki .......... A61H 23/0245 601/46 |

(Continued)

FOREIGN PATENT DOCUMENTS

| JP | 2014166304 A * | 9/2014 | ............ A45D 26/00 |
| JP | 2018-149343 A | 9/2018 | |

(Continued)

OTHER PUBLICATIONS

English translation for KR 101642248, machine translated by espacenet.com, translated on Jun. 27, 2023.*

(Continued)

*Primary Examiner* — Tu A Vo
(74) *Attorney, Agent, or Firm* — Birch, Stewart, Kolasch & Birch, LLP

(57) ABSTRACT

A skin care device according to an embodiment includes a main body and a head part connected to the main body, wherein the head part includes a housing in which an upper portion thereof is open, and including an accommodation space therein, an electrode part disposed in the housing, a plurality of light emitting elements disposed in the housing and spaced apart from the electrode part, and a cover part for shielding of the open upper region of the housing, wherein the cover part includes a hole corresponding to the electrode part, a part of the electrode part protrudes from an upper surface of the cover part via the hole, and an upper surface of the electrode part facing a skin of a user includes a convex curved surface toward the skin.

20 Claims, 11 Drawing Sheets

(51) Int. Cl.
*A61N 5/06* (2006.01)
*A61N 1/32* (2006.01)
*A61H 23/02* (2006.01)
*A61N 1/30* (2006.01)

(52) U.S. Cl.
CPC ............ *A61N 1/0428* (2013.01); *A61N 1/30* (2013.01); *A61N 1/303* (2013.01); *A61N 1/328* (2013.01); *A61N 5/0616* (2013.01); *A61H 2201/0153* (2013.01); *A61H 2201/10* (2013.01); *A61H 2201/105* (2013.01); *A61H 2201/1207* (2013.01); *A61H 2201/5025* (2013.01); *A61H 2205/022* (2013.01); *A61N 2005/0644* (2013.01); *A61N 2005/0662* (2013.01); *A61N 2005/0663* (2013.01); *A61N 2005/0664* (2013.01)

(58) Field of Classification Search
CPC .......... A61H 23/02–04; A61H 2023/002–029; A61H 2205/022; A61H 2201/1207; A61H 2201/5025; A61N 1/0408; A61N 1/328; A61N 5/0616; A61N 2005/0663; A61N 2005/0664; A61N 1/30; A61N 1/0428; A61N 1/303; A61N 2005/0644; A61N 2005/0662
See application file for complete search history.

(56) References Cited

U.S. PATENT DOCUMENTS

| | | | | |
|---|---|---|---|---|
| 2008/0125680 | A1* | 5/2008 | Richmond | A61H 23/0263 601/72 |
| 2012/0165710 | A1* | 6/2012 | Nichols | A61H 23/0263 601/72 |
| 2015/0100002 | A1* | 4/2015 | Choi | A61N 7/00 604/20 |
| 2016/0089537 | A1* | 3/2016 | Yamazaki | A61N 1/328 601/2 |
| 2017/0189670 | A1* | 7/2017 | Brunson | A61H 7/001 |
| 2018/0361137 | A1* | 12/2018 | Kern | A61N 1/322 |
| 2020/0253811 | A1* | 8/2020 | Alexander | A61L 31/14 |
| 2022/0203116 | A1* | 6/2022 | Park | A61N 1/08 |

FOREIGN PATENT DOCUMENTS

| | | |
|---|---|---|
| KR | 10-2009-0091496 A | 8/2009 |
| KR | 10-1139808 B1 | 4/2012 |
| KR | 10-2013-0106019 A | 9/2013 |
| KR | 10-2014-0001514 A | 1/2014 |
| KR | 10-1441016 B1 | 9/2014 |
| KR | 101451961 B1 * | 10/2014 |
| KR | 101580238 B1 * | 12/2015 |
| KR | 10-1642248 B1 | 7/2016 |
| KR | 101642248 B1 * | 7/2016 |
| KR | 10-1715647 B1 | 3/2017 |

OTHER PUBLICATIONS

English translation for KR 101451961, machine translated by espacenet.com, translated on Jun. 28, 2023.*

English translation for JP 2014166304, machine translated by Search Clarivate Analytics, translated on Jun. 29, 2023.*

English translation for KR 101580238, machine translated by Search Clarivate Analytics, translated on Jun. 29, 2023.*

* cited by examiner

SKIN CARE DEVICE

CROSS-REFERENCE TO RELATED APPLICATIONS

This application claims priority to and the benefit of Korean Patent Application No. 2019-0145605, filed on Nov. 14, 2019, the disclosure of which is incorporated herein by reference in its entirety.

TECHNICAL FIELD

Embodiments relate to a skin care device.

BACKGROUND

Human skin may be contaminated by external activities, and wrinkles may be formed due to aging, hormonal changes, and the like. Recently, as interest in the skin has increased, a cleansing device that may effectively remove skin contamination, and several devices for beauty and anti-aging have been developed.

For example, a device has been developed that provides high frequency and infrared energy to the skin. The device may be a device that applies thermal energy to the skin, may improve elasticity of an applied skin region by applying thermal energy to the skin, and may effectively provide a beauty product inside the skin.

In addition, devices have been developed that provide sound waves and light beams to the skin. As an example, sonophoresis and laserporation devices have been developed that may use ultrasonic waves or laser light to provide the beauty product inside the skin. The devices may use ultrasonic waves or laser light to form a path for injecting cosmetics into the skin, which may increase a skin penetration rate of a skin beauty product.

In addition, devices have been developed that physically provide beauty products to the skin using less current. As an example, the devices are devices that use iontophoresis, electroporation, electroosmosis, etc., and are devices that may effectively provide an active ingredient inside the skin by applying current to charged beauty products and neutral beauty products.

That is, various devices have been developed that may provide skin beauty and anti-aging functions by using light energy, sound waves, current, vibration, and the like.

In general, a beauty device using high frequency is a device that applies an electrical stimulation to the skin to care for the skin, and may provide the electrical stimulation in a high frequency band to the skin. Explaining the high frequency device in detail, when the high frequency is applied to the skin, deep heat which is frictional heat may be generated while intracellular ions move to an anode from a cathode. The deep heat is about 40° C. to about 50° C., and the skin may be sterilized by the deep heat. In addition, the deep heat may dilate blood vessels inside the skin and facilitate a metabolic function, and there is an effect that the beauty product may be effectively provided inside the skin.

To this end, the device using the high frequency may include an electrode formed on a surface thereof, and the electrode may be in contact with the skin of a user. However, when the device is used in a flexed skin region such as a face, a contact between the electrode and the skin may not be smooth. Accordingly, there is a problem that the high frequency is excessively provided in some regions to damage the skin such as burns, and the high frequency is not provided in some other regions.

In addition, in general, the electrode of the device has a shape protruding from the surface of the device for contact with the skin. In this case, when the user grasps the device and massages the skin, there is a problem that it is difficult to naturally massage the flexed skin region such as both cheeks, a chin, and both eye rims by the protruding electrode.

In addition, the device generally has a structure in which a head part that generates the high frequency and a body connected to the head part are integrally formed. Accordingly, when the user uses other functions than the high frequency for skin care, there is a problem that a new device different from the device should be provided.

Therefore, a new skin care device capable of solving the above-described problems is required.

SUMMARY

Technical Problem

An embodiment provides a skin care device capable of beautifying or treating skin by providing a set current to the skin.

In addition, the embodiment provides a skin care device capable of providing light in various wavelength bands to the skin.

In addition, the embodiment provides a skin care device capable of massaging a skin region in contact with the device by generating uniform vibrations.

In addition, the embodiment provides a skin care device capable of effectively providing light, vibration, and current in various wavelength bands to the skin by effectively contacting the skin.

Technical Solution

A skin care device according to an embodiment includes a main body and a head part connected to the main body, wherein the head part includes a housing in which an upper portion thereof is open, and including an accommodation space therein, an electrode part disposed in the housing, a plurality of light emitting elements disposed in the housing and spaced apart from the electrode part, and a cover part for shielding of the open upper region of the housing, wherein the cover part includes a hole corresponding to the electrode part, a part of the electrode part protrudes from an upper surface of the cover part via the hole, and an upper surface of the electrode part facing a skin of a user includes a convex curved surface toward the skin.

Advantageous Effects

A skin care device according to an embodiment may include a main body and a head part connected to the main body, and the head part may be provided detachably from the main body. Accordingly, when the head part is damaged or fails, only the head part may be replaced, and thus it is possible to have high efficiency. In addition, when a user wants to use an additional function other than the function included in the provided head part, it is not necessary to separately purchase or use a skin care device for the additional function, and the head part including the additional function may be used in connection with the main body. Accordingly, the user may use the skin care device economically and efficiently.

In addition, the skin care device according to the embodiment includes a plurality of electrode parts, and the electrode parts may provide a set current to a skin of the user. Specifically, the skin care device may provide at least one selected from a high frequency current, a galvanic current, and a microcurrent. Accordingly, it is possible to form deep heat in the skin of the user, to accelerate generation of adenosine triphosphate (ATP), and to effectively provide cosmetics or drugs inside the skin.

In addition, the electrode part according to the embodiment may include a curved surface. Specifically, in the electrode part, an upper surface of a plurality of contact portions in contact with the skin of the user may include a curved surface. Further, a surface of the head part in contact with the skin of the user, for example, a surface of a cover part may include a curved surface. Accordingly, when the user rolls the skin care device on the skin, it is possible to effectively massage the skin of the user.

Further, since the surface of the electrode part and/or the cover part according to the embodiment includes a curved surface, it is possible to effectively adhere to a relatively flexed region such as a chin, both cheeks, and eye rims, and to maximize a massage effect on the region.

Furthermore, the electrode parts according to the embodiment may have different heights. Specifically, the electrode parts may include a first electrode part and a second electrode part disposed around the first electrode part, and a height of the second electrode part may be provided lower than that of the first electrode part. Accordingly, the first and second electrode parts may not be spaced apart from the skin on the flexed skin region, and may be effectively in contact with the skin.

In addition, the skin care device according to the embodiment may provide light in various wavelength bands to the skin of the user. Specifically, the skin care device may provide at least one of red, orange, and green light to the skin of the user. Accordingly, it is possible to provide cosmetic effects that may induce formation of collagen on the skin of the user and reduce fine wrinkles. In addition, the skin care device may provide a therapeutic effect such as soothing a region to which light of various wavelength bands is applied and alleviating a formed inflammation.

In addition, the skin care device according to the embodiment may provide vibration to the skin of the user. Accordingly, the skin of the user may be massaged, and at the same time, contaminants on the skin of the user, wastes in pores, and the like may be removed from the skin. In addition, the vibration may cause cracks in a stratum corneum formed on the surface of the skin or expand a gap between the stratum corneums to provide a movement path of cosmetics or drugs. Therefore, the skin care device may be used to effectively provide the cosmetics or the drugs inside the skin.

DETAILED DESCRIPTION OF THE EMBODIMENTS

Figure 1:
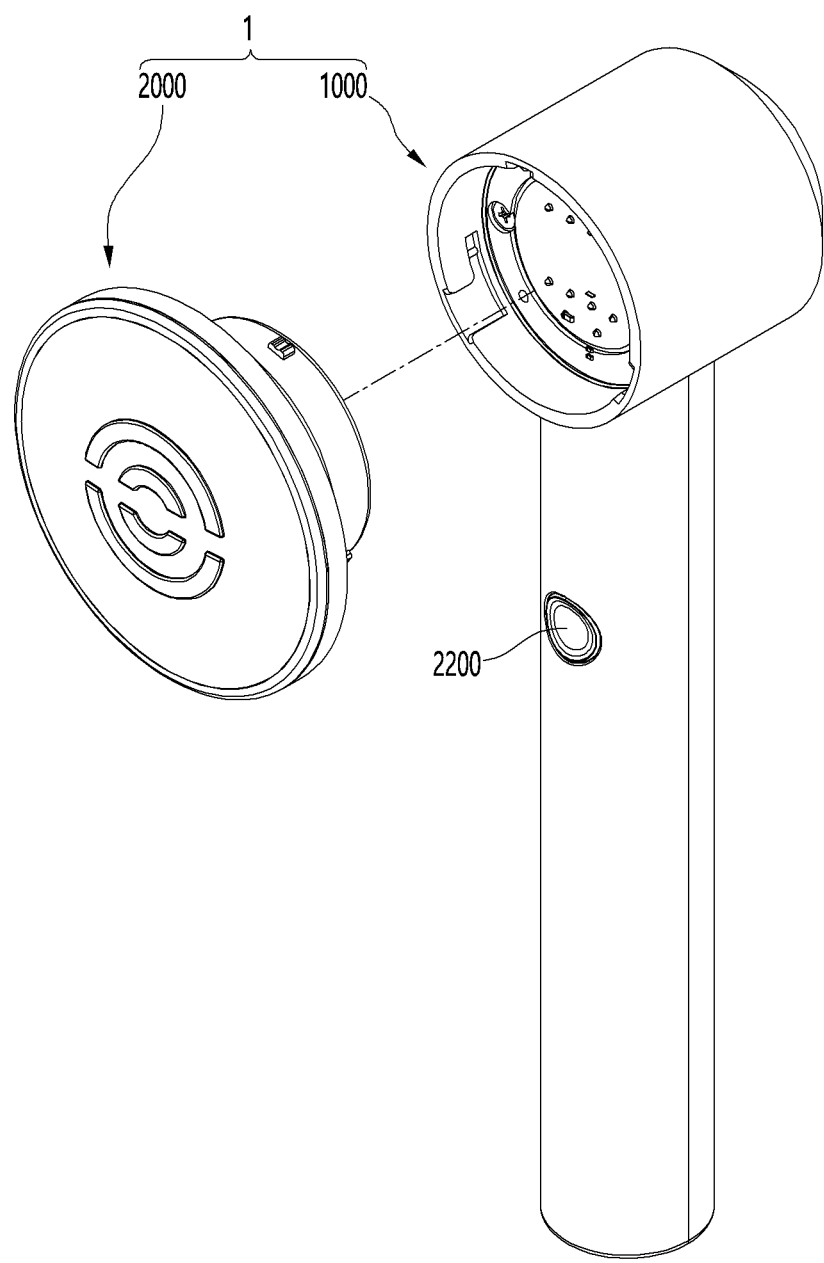
FIG. 1 is an exploded perspective view of a cleaning device according to an embodiment.

Hereinafter, embodiments of the present invention will be described in detail with reference to the accompanying drawings.

However, the spirit and scope of the present invention is not limited to a part of the embodiments described, and may be implemented in various other forms, and within the spirit and scope of the present invention, one or more of the elements of the embodiments may be selectively combined and replaced.

In addition, unless expressly otherwise defined and described, the terms used in the embodiments of the present invention (including technical and scientific terms may be construed the same meaning as commonly understood by one of ordinary skill in the art to which this invention belongs, and the terms such as those defined in commonly used dictionaries may be interpreted as having a meaning that is consistent with their meaning in the context of the relevant art.

In addition, the terms used in the embodiments of the present invention are for describing the embodiments and are not intended to limit the present invention. In this specification, the singular forms may also include the plural forms unless specifically stated in the phrase, and may include at least one of all combinations that may be combined in A, B, and C when described in "at least one (or more) of A (and), B, and C".

In addition, in describing the elements of the embodiments of the present invention, the terms such as first, second, A, B, (A, and (b) may be used. These terms are only used to distinguish the elements from other elements, and the terms are not limited to the essence, order, or order of the elements. Further, when an element is described as being "connected", "coupled", or "connected" to another element, it may include not only when the element is directly "connected" to, "coupled" to, or "connected" to other elements, but also when the element is "connected", "coupled", or "connected" by another element between the element and other elements.

In addition, when described as being formed or disposed "on (over)" or "under (below)" of each element, the "on (over)" or "under (below)" may include not only when two elements are directly connected to each other, but also when one or more other elements are formed or disposed between two elements. Further, when expressed as "on (over)" or "under (below)", it may include not only the upper direction but also the lower direction based on one element.

In addition, before describing the embodiment of the invention, the first direction may refer to the x-axis direction shown in the drawings, and the second direction is a direction different from the first direction. As an example, the second direction may refer to the y-axis direction shown in the drawings in a direction perpendicular to the first direction. Further, the horizontal direction may refer to a direction perpendicular to at least one of the first and second directions. For example, the horizontal direction may be a direction perpendicular to the x-axis and y-axis directions of the drawing.

Figure 2:
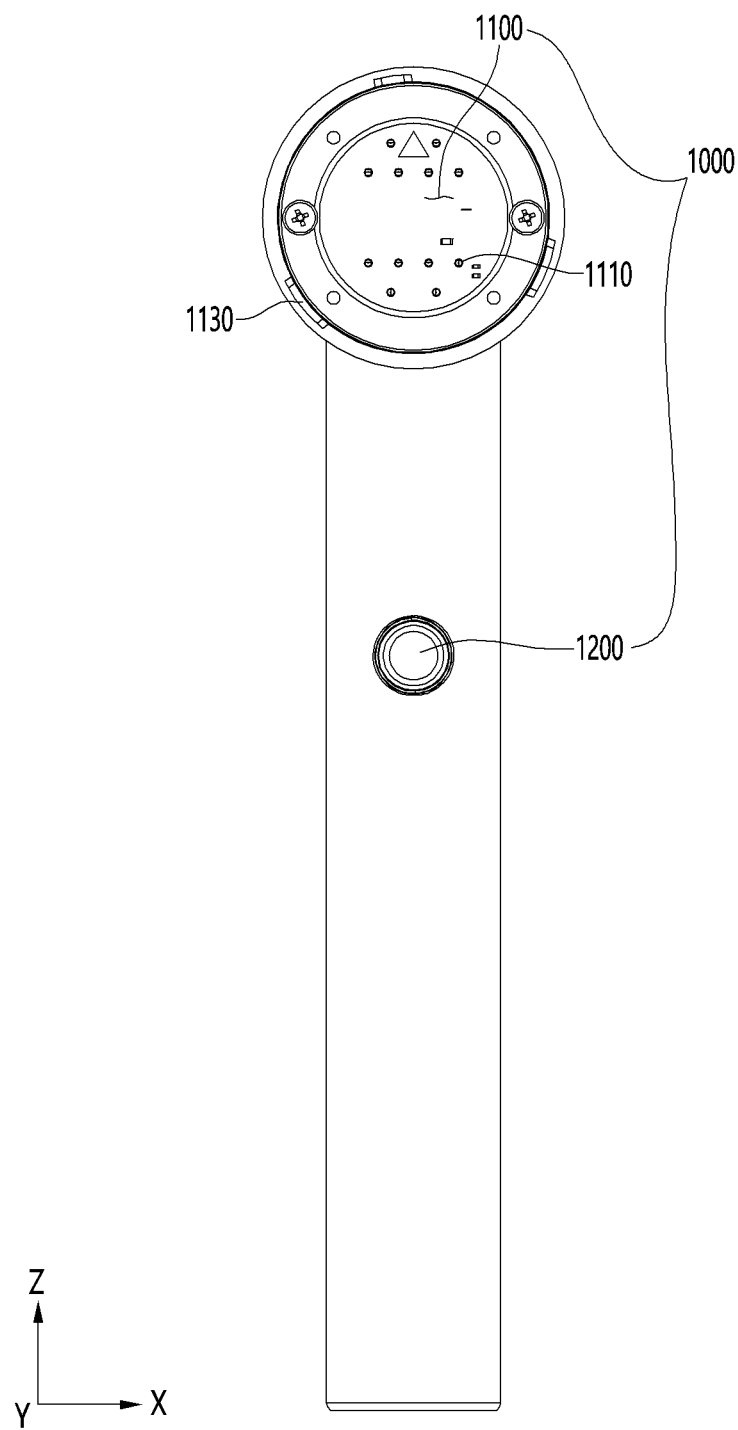
FIG. 2 is a front view of a main body according to an embodiment.
Figure 3:
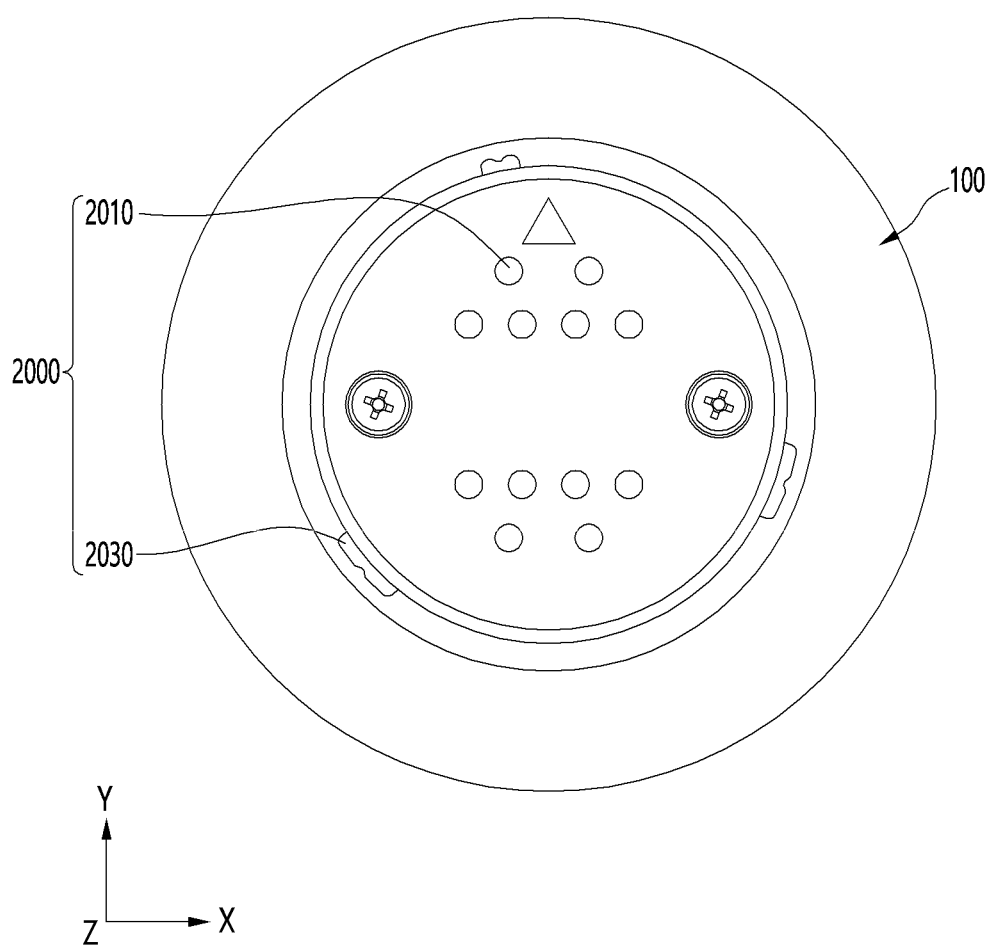
FIG. 3 is a bottom view of a head part according to an embodiment.

FIG. 1 is an exploded perspective view of a cleaning device according to an embodiment, FIG. 2 is a front view of a main body according to an embodiment, and FIG. 3 is a bottom view of a head part according to an embodiment.

Referring to FIGS. 1 to 3, a skin care device 1 according to an embodiment may include a main body 1000 and a head part 2000.

The main body 1000 may have a shape that is easy for a user to grasp by hand. The main body 1000 may have a shape extending in one direction. For example, the main body 1000 may have a shape extending in a vertical direction (z-axis direction). The main body 1000 may have a shape of a bar or stick such as a cylinder, polygonal prism, or the like that extends in one direction. Accordingly, the user may grasp the main body 1000 by hand to control a position of the skin care device 1.

The main body 1000 may include an accommodation space (not shown) therein. A battery (not shown) may be disposed in the accommodation space of the main body 1000. The battery may supply power to the skin care device 1. For example, the battery may supply power to the main body 1000 and the head part 2000 connected to the main body 1000, respectively. The battery may include one selected from primary batteries such as a manganese (Mn) battery, an alkaline battery, a mercury battery, a silver oxide battery, and the like. In addition, the battery may include one selected from secondary batteries such as a nickel-cadmium (Ni—Cd) battery, a nickel-hydrogen (Ni—MH) battery, and a lithium-ion (Li-ion) battery.

When the skin care device 1 includes a rechargeable battery, a cover (not shown) for detaching the battery may be disposed on the outside of the main body 1000. Alternatively, when the battery is disposed inside the main body 1000 and is difficult to detach, the skin care device 1 may include a charging terminal portion (not shown). The charging terminal portion may be electrically connected to the battery disposed inside the main body 1000, and a part of the charging terminal portion may be exposed to the outside of the main body 1000. The user may connect a USB port, a cable, or the like for charging the battery to the exposed charging terminal portion to charge the battery. Alternatively, the skin care device 1 described above may be provided so as to be wirelessly rechargeable. In detail, the skin care device 1 may be provided so as to be wirelessly rechargeable by a coil or the like disposed in the main body 1000. For example, the skin care device 1 may charge the battery by a wireless charging method such as a self-resonant method, a magnetic induction method, and the like.

A switch 2200 may be disposed on the outside of the main body 1000. The switch 2200 may be a physical switch that includes an elastic body such as a spring. In addition, the switch 2200 may be an electric switch on which a touch electrode or the like is formed. The user may control the skin care device 1 via the switch 2200.

In addition, an indicator lamp (not shown) may be disposed on the outside of the main body 1000. For example, the indicator lamp may be disposed to be adjacent to the switch 2200. The indicator lamp may display a status of the skin care device. For example, when the user operates the skin care device 1 via the switch 2200 (on mode), the indicator lamp may emit light in a set color. In addition, when the user terminates the operation of the skin care device 1 via the switch 2200 or the operation of the skin care device 1 is terminated by a set time or the like (off mode), the indicator lamp does not emit light, or may emit light of a color different from that of the on mode.

A speaker (not shown) may be disposed in the accommodation space of the main body 1000. The speaker may output a state of the skin care device 1 as sound. For example, when the user operates the skin care device 1 via the switch 2200 (on mode), the speaker may output a sound notifying the start of operation. In addition, when the operation of the skin care device 1 is terminated (off mode), the speaker may output a sound of the end of operation.

The main body 1000 may include a first recess 1100 formed on one side thereof. The first recess 1100 may have a concave shape in an internal direction of the main body 1000 from one side of the main body 1000.

The main body 1000 may include a first terminal 1110. The first terminal 1110 may be disposed on a lower surface of the first recess 1100. The first terminal 1110 may be electrically connected to the battery disposed in the main body 1000.

In addition, the main body 1000 may include at least one first groove 1130. The first groove 1130 may be disposed on an inner circumferential surface of the first recess 1100. The first groove 1130 may have a concave shape toward an outer circumferential surface from the inner circumferential surface of the first recess 1100.

The main body 1000 may be connected to the head part 2000. The main body 1000 may be physically connected to the head part 2000. For example, the first recess 1100 of the main body 1000 may have a shape corresponding to the head part 2000, and may be provided at a predetermined depth corresponding to the head part 2000. A part of the head part 2000 may be inserted into the first recess 1100 to connect to the main body 1000.

The head part 2000 may include at least one first protrusion 2030. The first protrusion 2030 may be disposed on an outer surface of the head part 2000. The first protrusion 2030 may be disposed in a region corresponding to the first groove 1130 of the main body 1000. In addition, the first protrusion 2030 may be provided in a number corresponding to the first groove 1130. The head part 2000 may be physically connected by inserting the first protrusion 2030 into the first groove 1130.

In addition, the head part 2000 may be electrically connected to the main body 1000. For example, the head part 2000 may include a second terminal 2010 disposed on the lower surface thereof facing the lower surface of the first recess 1100. The second terminal 2010 may be disposed in a region corresponding to the first terminal 1110, and may be in contact with the first terminal 1110. Specifically, the second terminal 2010 may be in contact with the first terminal 1110 in a process of physically connecting the head part 2000 and the main body 1000, for example, a process of physically connecting the first protrusion 2030 and the first groove 1130. Accordingly, the first terminal 1110 may be electrically connected to the second terminal 2010, and the main body 1000 and the head part 2000 may be electrically connected to each other. Therefore, the battery disposed in the main body 1000 may supply power to the head part 2000.

Figure 4:
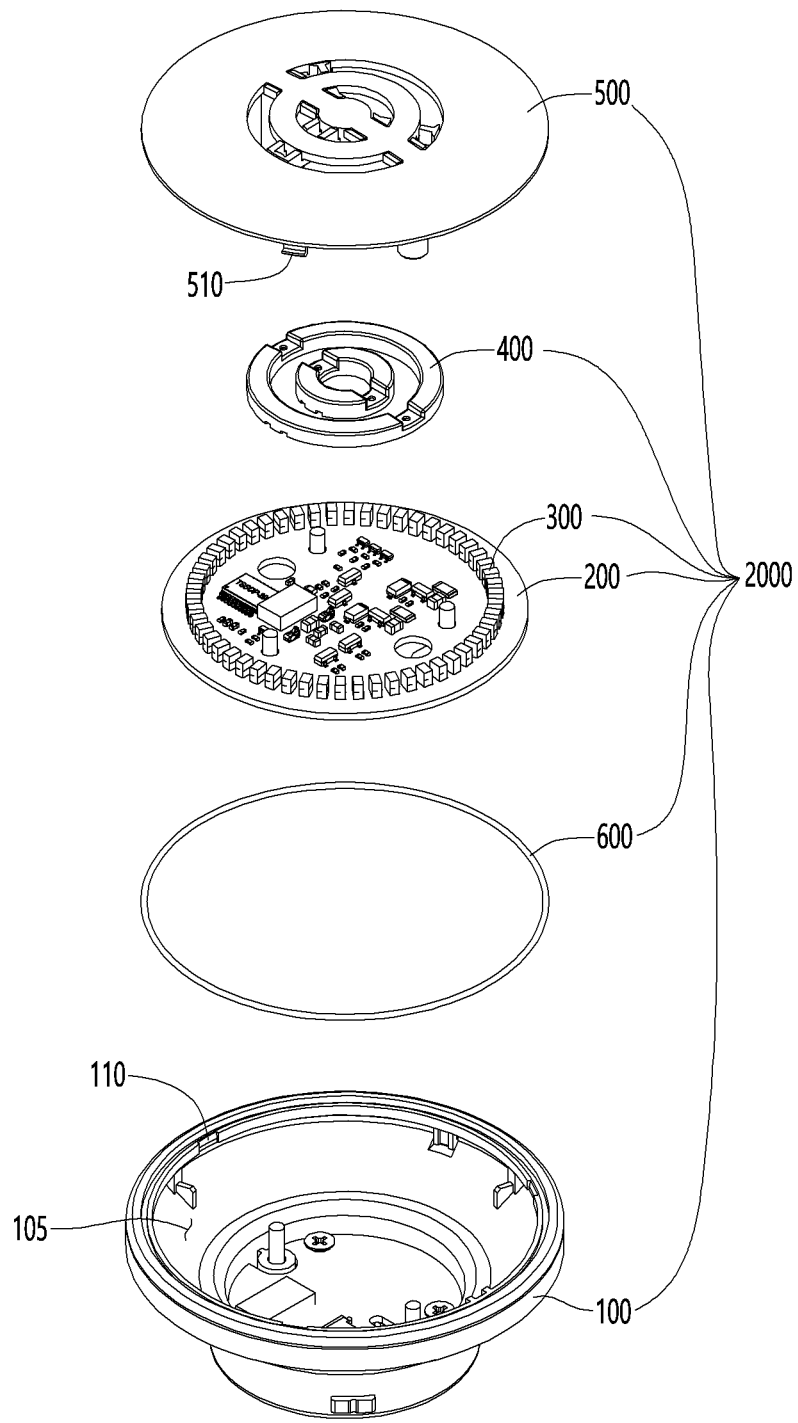
FIG. 4 is an exploded perspective view of a head part according to an embodiment.

FIG. 4 is an exploded perspective view of a head part according to an embodiment. Referring to FIG. 4, a head part 2000 according to an embodiment may include a housing 100, a substrate 200, a light emitting element 300, an electrode part 400, and a cover part 500.

The housing 100 may have an open upper portion, and may include an accommodation space 105 therein. For example, the housing 100 may include a through-hole formed on an upper surface thereof, and the upper portion thereof may be open by the through-hole. The substrate 200, the light emitting element 300, and the electrode part 400 may be disposed in the accommodation space 105 of the housing 100.

The substrate 200 may be disposed in the housing 100. The substrate 200 may be a circuit board on which a circuit pattern is printed on an insulator. The substrate 200 may include at least one of a printed circuit board (PCB) with a resin material, a metal core PCB (MCPCB), a nonflexible PCB, a flexible PCB (FPCB), and a ceramic material. The substrate 200 may include a resin material layer or a ceramic-based layer, and the resin material may be formed of a silicone, an epoxy resin, a thermosetting resin containing a plastic material, or a material having high heat resistance and high light resistance. The ceramic material may include co-fired low temperature cofired ceramics (LTCC) or high temperature cofired ceramics (HTCC).

The substrate 200 may have a plurality of via structures. The via structure of the substrate 200 may electrically connect electrode patterns formed on an upper surface and a lower surface of the substrate 200. In addition, although not shown in the drawing, a protective element, a transistor, a resistor and the like may be disposed on the substrate 200.

The substrate 200 may be disposed at a set position. Specifically, the substrate 200 may be disposed fixedly at the set position in the housing 100. As an example, the housing 100 may include at least one fixing portion (not shown) extending toward the substrate 200 from a lower surface of the housing 100, and the substrate 200 may include at least one hole (not shown) corresponding to the fixing portion. The fixing portion of the housing 100 may be disposed to be inserted into the hole of the substrate 200, and accordingly, the substrate 200 may be fixed on the housing 100.

In addition, the substrate 200 may be more firmly fixed on the housing 100 by a separate fastening member (not shown). For example, the fixing portion of the housing may include a fastening hole (not shown) formed on an upper surface of the fixing portion. The fastening hole is a hole penetrated toward a lower surface from the upper surface of the fixing portion, and an inner circumferential surface thereof may be provided in a shape of a female thread, and the fastening member may be provided in a shape of a male thread. That is, the substrate 200 may be firmly fixed on the housing 100 by the fastening member to be fastened after the hole of the substrate 200 is inserted into the fixing portion of the housing 100.

A plurality of light emitting elements 300 may be disposed in the housing 100. The plurality of light emitting elements 300 may be disposed on the substrate 200. The plurality of light emitting elements 300 may be electrically connected to the substrate 200. The plurality of light emitting elements 300 may be disposed on the upper surface of the substrate 200. The plurality of light emitting elements 300 may be disposed in an edge region of the substrate 200. The plurality of light emitting elements 300 may be disposed around the electrode part 400 described later.

The plurality of light emitting elements 300 may emit light in a visible light band. More specifically, the plurality of light emitting elements 300 may emit light having a wavelength of about 400 nm or more as a visible light emitting element. For example, the plurality of light emitting elements 300 may emit light of at least one wavelength band of green light having a wavelength band of about 450 nm to about 580 nm, orange light having a wavelength band of about 590 nm to about 620 nm, and red light having a wavelength band of about 620 nm to about 750 nm.

The electrode part 400 may be disposed in the housing 100. The electrode part 400 may be disposed on the substrate 200. The electrode part 400 may contain a material that is harmless to the human body. Specifically, the electrode part 400 may contain a conductive metal material of which shape is not deformed by contact pressure with the skin. As an example, the electrode part 400 may include at least one metal of aluminum (Al), copper (Cu), zinc (Zn), iron (Fe), nickel (Ni), chromium (Cr), silver (Ag), gold (Au), platinum (Pt), stainless steel (SUS), and alloys thereof.

The electrode part 400 may be electrically connected to the substrate 200 and may be in contact with the skin of the user. The electrode part 400 may provide at least one of a high frequency current, a galvanic current, and a microcurrent to the skin of the user. Descriptions of the electrode part 400 will be described in more detail with reference to the drawings described later.

The cover part 500 may be disposed on the housing 100. The cover part 500 may be disposed on an open upper region of the housing 100. The cover part 500 may be translucent or opaque, and may include a material that may transmit light emitted from the light emitting element 300. In addition, the cover part 500 may include a material that is lightweight and may be prevented from being damaged by an external impact or contact. As an example, the cover part 500 may include at least one of materials such as resin, ceramics, and metal, and accordingly, it may transmit the light emitted from the light emitting element 300, and it may have improved reliability against an external environment.

The cover part 500 may shield the open upper region of the housing 100. The cover part 500 may be coupled to the housing 100 to shield the open region. For example, the cover part 500 may have a shape corresponding to the open upper region of the housing 100, and may include at least one coupling latch 510 disposed on an outer surface thereof. The coupling latch 510 may have a shape protruding toward an inner circumferential surface of the housing 100 such as a horizontal direction, a vertical direction, and a diagonal direction on the outer surface of the cover part 500. In addition, the housing 100 may include at least one coupling groove 110 disposed on the inner circumferential surface thereof. The coupling groove 110 may have a shape corresponding to the coupling latch 510 and may be disposed at a corresponding position.

That is, the cover part 500 may be coupled to the housing 100 in a process of shielding the open upper region of the housing 100. Specifically, in the process in which the cover part 500 shields the upper portion of the housing 100, the coupling latch 510 may be engaged with the coupling groove 110, and the cover part 500 may be tightly coupled to the housing 100.

In addition, the cover part 500 may include a hole into which a part of the electrode part 400 is inserted. Here, the hole of the cover part 500 may be a hole penetrating an upper surface 501 and a lower surface of the cover part 500. The hole of the cover part 500 may be disposed at a position corresponding to the electrode part 400, and may have a corresponding shape. Accordingly, a part of the electrode part 400 may be disposed to be inserted into the hole of the cover part 500, and may be exposed to the outside. The cover part 500 will be described in more detail with reference to the drawings described later.

The skin care device 1 according to the embodiment may include a sealing member 600 disposed between the housing 100 and the cover part 500. The sealing member 600 may be disposed in a region overlapped with a periphery of the inner circumferential surface of the housing 100 and a periphery of the lower surface of the cover part 500. The sealing member 600 may have an O-ring shape. In addition, the sealing member 600 may be disposed in direct contact with the housing 100 and the cover part 500.

The sealing member 600 may include an elastic material. As an example, the sealing member 600 may include a resin material such as nitrile butadiene rubber (NBR), ethylene propylene (EPDM), fluorinated rubber (FPM), silicone, and the like, and an elastic rubber material.

Accordingly, the sealing member 600 may shield a space between the housing 100 and the cover part 500. Specifically, in a process of coupling the cover part 500 and the housing 100, the sealing member 600 may be elastically deformed, and in the process, the space between the housing 100 and the cover part 500 may be shielded. Accordingly, it is possible to prevent moisture, dust, foreign matter, etc. from flowing into the accommodation space 105 of the housing 100 via the space between the housing 100 and the cover part 500.

The skin care device 1 according to the embodiment may include a vibrating member 700. The vibrating member 700 may be disposed in the accommodation space 105 of the housing 100. The vibrating member 700 may be electrically connected to the substrate 200 and may generate vibration energy. For example, the vibrating member 700 may generate vibration energy toward a surface of the head part 2000, for example, toward the upper surface 501 of the cover part 500. The vibrating member 700 may generate wave energy of about 1 Hz to about 10000 Hz. That is, the vibrating member 700 may generate low-frequency or medium-frequency energy toward the upper surface 501 of the cover part 500, and may provide the energy on the skin of the user in contact with the head part 2000. Accordingly, it possible to massage the skin region in contact with the head part 2000, and simultaneously, to provide effects such as increase of blood flow, increase of metabolism, and strengthening of muscle strength.

As described above, the cover part 500 according to the embodiment may have a structure capable of coupling to and separating from the housing 100. However, the embodiment is not limited thereto, and the cover part 500 and the housing 100 may be integrally formed to omit the cover part 500. In this case, the above-mentioned hole may be formed on a surface of the housing 100 facing and contacting the skin, for example, on the upper surface of the housing 100, and a part of the electrode part 400 may be inserted into the hole of the housing 100 to be exposed to the outside. In this case, the upper surface of the housing 100 corresponding to the light emitting element 300 may be provided translucently or opaquely, and may transmit the light emitted from the light emitting element 300.

Figure 5:
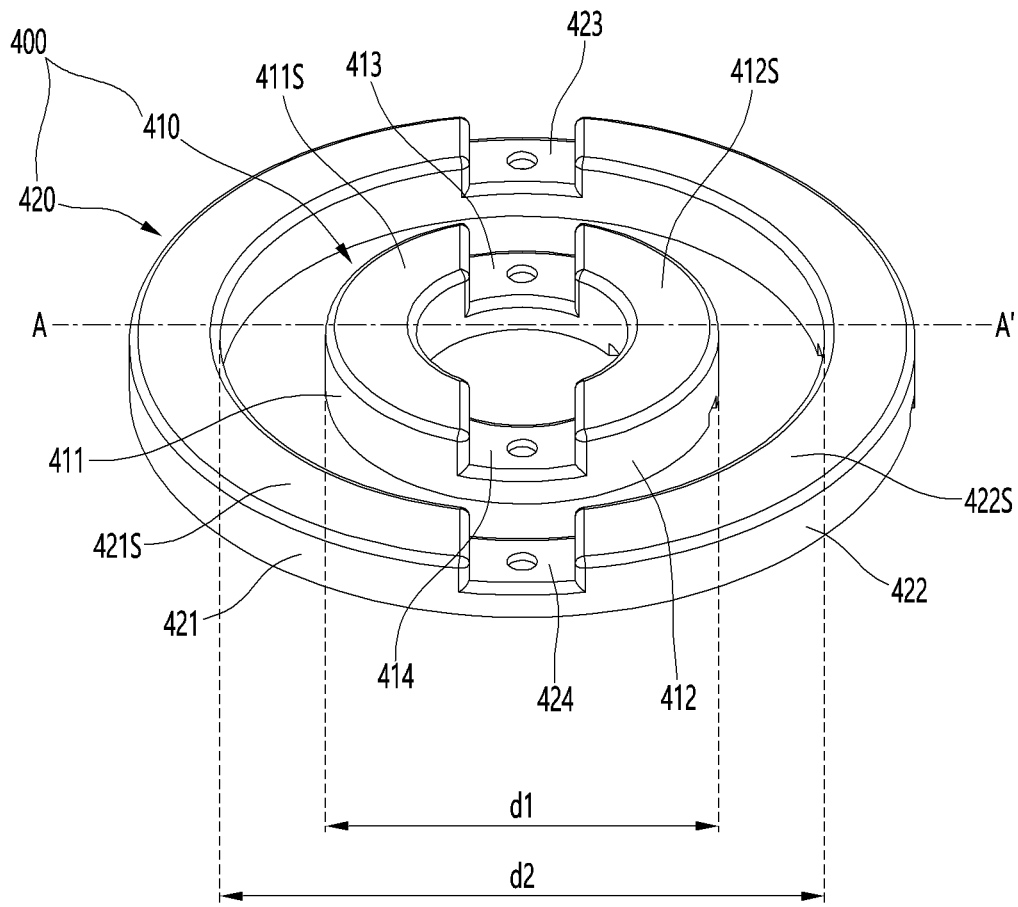
FIG. 5 is a perspective view of an electrode part according to an embodiment.
Figure 6:
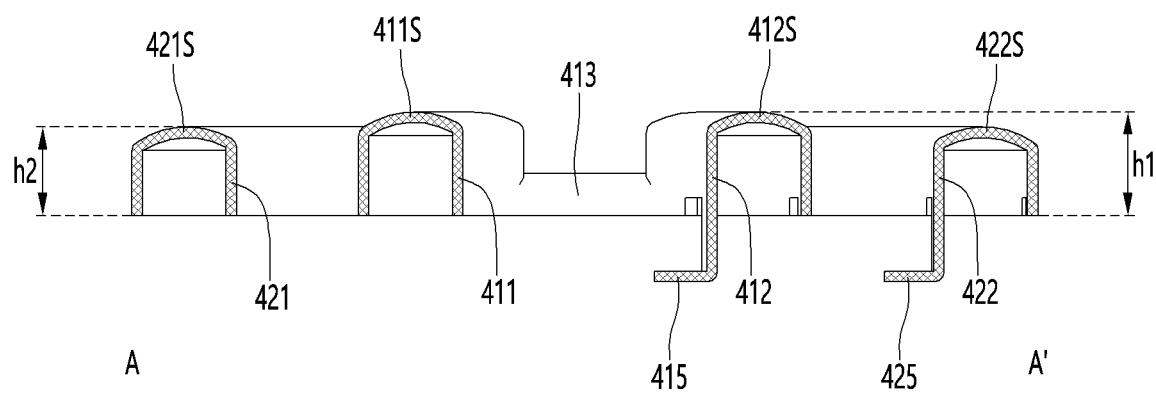
FIG. 6 is a cross-sectional view showing a cross section taken along line A-A' of FIG. 5.
Figure 7:
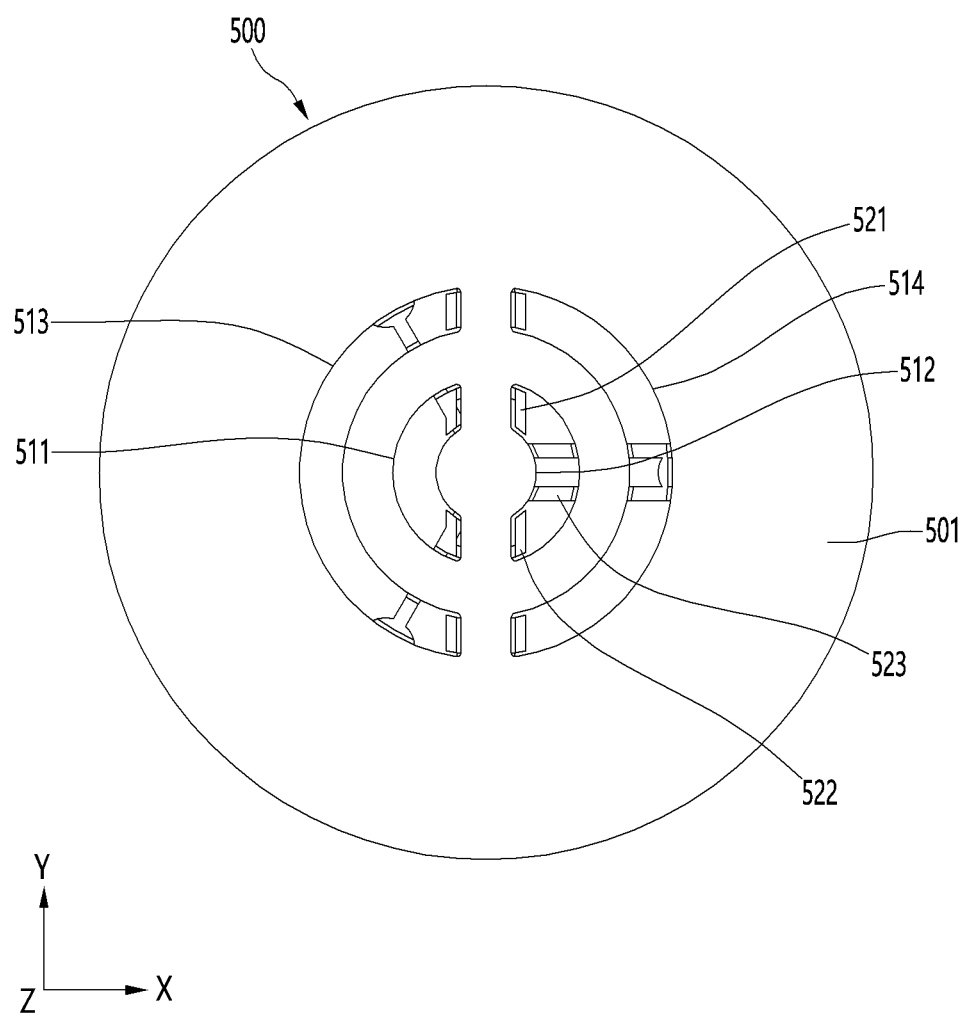
FIG. 7 is a top view of a cover part according to an embodiment.

FIG. 5 is a perspective view of an electrode part according to an embodiment, and FIG. 6 is a cross-sectional view showing a cross section taken along line A-A' of FIG. 5. In addition, FIG. 7 is a top view of a cover part according to an embodiment. The electrode part and the cover part according to the embodiment will be described in more detail with reference to FIGS. 5 to 7.

Referring to FIGS. 5 and 6, the electrode part 400 may include a plurality of electrode parts 410 and 420. For example, the electrode part 400 may include a first electrode part 410 and a second electrode part 420 that are spaced apart from each other. The second electrode part 420 may be disposed surrounding a periphery of the first electrode part 410, and may be disposed to be spaced apart from the first electrode part 410 at equal distances.

The first electrode part 410 may have an annular planar shape, and may include a first diameter d1 defined as a diameter of an outer circumferential surface. In addition, the first electrode part 410 has a predetermined thickness, and a recess may be formed on a lower surface thereof. The recess may have a concave shape toward an upper surface from the lower surface of the first electrode part 410. That is, the first electrode part 410 may have a U-shape of which cross-sectional shape is turned upside down in an opposite direction. Accordingly, a weight of the first electrode part 410 may be reduced, and a total weight and manufacturing cost of the head part 2000 may be reduced.

The first electrode part 410 may include a first contact portion 411 and a second contact portion 412 exposed to the outside of the skin care device 1. The first contact portion 411 and the second contact portion 412 may be electrodes that are in contact with the skin of the user.

The first contact portion 411 and the second contact portion 412 may have shapes corresponding to each other. As an example, the first contact portion 411 and the second contact portion 412 may have a U-shape of which cross-sectional shape is turned upside down in an opposite direction.

The first contact portion 411 and the second contact portion 412 may be spaced apart from each other while facing each other in a first direction (x-axis direction). In addition, the first contact portion 411 and the second contact portion 412 may be symmetrical with each other with respect to a virtual line in a second direction (y-axis direction).

The first contact portion 411 may include an upper surface facing and contacting the skin of the user, and the upper surface of the first contact portion 411 may be defined as a first contact surface 411S. In addition, the second contact portion 412 may include an upper surface facing and contacting the skin of the user, and the upper surface of the second contact portion 412 may be defined as a second contact surface 412S. The first contact surface 411S and the second contact surface 412S may be disposed above the upper surface 501 of the cover part 500. Accordingly, the first contact portion 411 and the second contact portion 412 may be in contact with the skin of the user, and may provide at least one of a high frequency current, a galvanic current, and a microcurrent to the skin.

The first electrode part 410 may have a first height h1. Here, the first height h1 may be defined by a height from the lower surface of the first electrode part 410 to the uppermost portion of the first electrode part 410. Specifically, the first height h1 may refer to a vertical height from a lower surface of the first contact portion 411 in which a first terminal portion 415 described later is not disposed to the uppermost portion of the first and the second contact portions 411 and 412. At this time, the first height h1 of the first contact portion 411 and the second contact portion 412, that is, the maximum height may be the same.

The first electrode part 410 may include a curved surface. For example, an upper surface of the first electrode part 410 facing the skin of the user may include a curved surface. Specifically, the first contact portion 411 and the second contact portion 412 in contact with the skin of the user may include a curved surface. More specifically, the first contact surface 411S and the second contact surface 412S may include a curved surface. The first contact surface 411S and the second contact surface 412S may be curved surfaces that are convex in a direction of the skin of the user. At this time, the first contact surface 411S and the second contact surface 412S may have the same curvature radius to each other.

For example, the curvature radius of the first contact surface 411S and the second contact surface 412S may be about 100 mm to about 200 mm. Specifically, the curvature radius of the first contact surface 411S and the second contact surface 412S may be about 120 mm to about 180 mm. When the curvature radius of the first contact surface 411S and the second contact surface 412S is less than about 100 mm, surfaces of the first and second contact portions 411 and 412 have a relatively large curvature R value, and thus a massage effect may be increased, but it is difficult to effectively provide current to the skin of the user. In addition, when the curvature radius of the first contact surface 411S and the second contact surface 412S exceeds about 200 mm, an effect of being able to massage the skin is reduced by a relatively small curvature value. Therefore, it is desirable to satisfy the range of the first contact surface 411S and the second contact surface 412S described above in consideration of effectively providing the current to the skin of the user, and simultaneously, of the massage effect by the first and second contact portions 411 and 412.

The first electrode part 410 may further include a first connecting portion 413 and a second connecting portion 414. The first connecting portion 413 and the second connecting portion 414 may be disposed at both ends of the first contact portion 411 and the second contact portion 412 respectively to connect the first contact portion. 411 and the second contact portion 412.

The first connecting portion 413 and the second connecting portion 414 may have shapes corresponding to each other. As an example, the first connecting portion 413 and the second connecting portion 414 may be spaced apart from each other while facing each other in the second direction (y-axis direction). In addition, the first connecting portion 413 and the second connecting portion 414 may be symmetrical with respect to a virtual line in the first direction (x-axis direction).

The first connecting portion 413 and the second connecting portion 414 may not be exposed to the outside of the skin care device 1. For example, the first connecting portion 413 and the second connecting portion 414 may have a form that is bent and extended in the direction of the substrate 200 from the both ends of each of the first contact portion 411 and the second contact portion 412.

The first connecting portion 413 and the second connecting portion 414 may have a lower height than the first contact portion 411 and the second contact portion 412. Upper surfaces of the first connecting portion 413 and the second connecting portion 414 may be disposed below the upper surface 501 of the cover part 500. The first connecting portion 413 and the second connecting portion 414 may be provided in a concave shape at both ends of each of the first contact portion 411 and the second contact portion 412.

The first and second connecting portions 413 and 414 may provide a space in which the cover part 500 may be disposed, and may be disposed below the cover part 500. Specifically, the cover part 500 may be disposed on the first and second connecting portions 413 and 414, which are a space between the first and second contact portions 411 and 412, and thus it is possible to have improved reliability in a central region of the head part 2000. In addition, the cover part 500 is disposed on the first and second connecting portions 413 and 414, and accordingly, the first electrode part 410 may be effectively supported. For example, a fixing protrusion (not shown) extending in an upper surface direction of the first and second connecting portions 413 and 414 may be formed on a lower surface of the cover part 500. A fixing groove (not shown) corresponding to the fixing protrusion may be formed on the upper surface of each of the first and second connecting portions 413 and 414. Accordingly, when the cover part 500 is connected to the housing 100, the fixing protrusion of the cover part 500 may be disposed to be inserted into the fixing groove, and accordingly, the first electrode part 410 may be fixedly disposed at a set position.

In addition, the embodiment may include the first terminal portion 415 that connects the first electrode part 410 and the substrate 200. The first terminal portion 415 may be extended in the direction of the substrate 200 from at least one configuration of the first contact portion 411, the second contact portion 412, the first connecting portion 413, and the second connecting portion 414. As an example, the first terminal portion 415 may be connected to the second contact portion 412, and may be extended in the direction of the substrate 200 from a lower surface of the second contact portion 412. The first terminal portion 415 may be in direct contact with the substrate 200, and may be electrically connected to the substrate 200, and the set current may be applied to the first electrode part 410 via the first terminal portion 415.

The second electrode part 420 may have a shape corresponding to the first electrode part 410. For example, the second electrode part 420 may have an annular planar shape and may include a second diameter d2 defined as a diameter of an inner circumferential surface. At this time, the second diameter d2 may be larger than the first diameter d1. In addition, the second electrode part 420 has a predetermined thickness, and a recess may be formed on a lower surface thereof. The recess may have a concave shape toward an upper surface direction from the lower surface of the second electrode part 420. That is, the second electrode part 420 may have a U-shape of which cross-sectional shape is turned upside down in an opposite direction. Accordingly, a weight of the second electrode part 420 may be reduced, and a total weight and manufacturing cost of the head part 2000 may be reduced.

The second electrode part 420 may include a third contact portion 421 and a fourth contact portion 422 exposed to the outside of the skin care device 1. The third contact portion 421 and the fourth contact portion 422 may be electrodes that are in contact with the skin of the user.

The third contact portion 421 and the fourth contact portion 422 may have shapes corresponding to each other. As an example, the third contact portion 421 and the fourth contact portion 422 may have a U-shape of which cross-sectional shape is turned upside down in an opposite direction.

The third contact portion 421 and the fourth contact portion 422 may be spaced apart from each other while facing each other in the first direction (x-axis direction). In addition, the third contact portion 421 and the fourth contact portion 422 may be symmetrical with each other with respect to a virtual line in the second direction (y-axis direction).

The third contact portion 421 may include an upper surface facing and contacting the skin of the user, and the upper surface of the third contact portion 421 may be defined as a third contact surface 421S. In addition, the fourth contact portion 422 may include an upper surface facing and contacting the skin of the user, and the upper surface of the fourth contact portion 422 may be defined as a fourth contact surface 422S. The third contact surface 421S and the fourth contact surface 422S may be disposed above the upper surface 501 of the cover part 500. Accordingly, the third contact portion 421 and the fourth contact portion 422 may be in contact with the skin of the user, and may provide at least one of a high frequency current, a galvanic current, and a microcurrent to the skin.

The second electrode part 420 may have a second height h2. Here, the second height h2 may be defined by a height from the lower surface of the second electrode part 420 to the uppermost portion of the second electrode part 420. Specifically, the second height h2 may refer to a vertical height from a lower surface of the third contact portion 421 in which a second terminal portion 425 described later is not disposed to the uppermost portion of the third and fourth contact portions 421 and 422. At this time, the second height h2 of the third contact portion 421 and the fourth contact portion 422, that is, the maximum height may be the same.

The maximum height of the second electrode 420 may differ from that of the first electrode 410. For example, the maximum height of the second electrode part 420 may be lower than that of the first electrode part 410. Specifically, the second height h2 which is the maximum height of the third contact portion 421 and the fourth contact portion 422, may be lower than the first height h1 which is the maximum height of the first contact portion 411 and the second contact portion 412.

For example, the second height h2 may be about 75% to about 95% of the first height h1. Specifically, the second height h2 may be about 80% to about 95% of the first height h1. Preferably, the second height h2 may be about 85% to about 90% of the first height h1.

When the second height h2 is less than about 75% of the first height h1, contact characteristics between the skin of the user and the contact portions 411, 412, 421, and 422 may be deteriorated. As an example, when using the skin care device 1 for beauty or treatment of a flexed region such as both cheeks, a chin, and both eye rims of the skin region of the user, the first and second contact portions 411 and 412 may be in contact with the skin by a relatively low second height h2, and the third and fourth contact portions 421 and 422 may be spaced apart from the skin of the user. In addition, as described above, the first and second contact portions 411 and 412 may be spaced apart from the skin, and the third and fourth contact portions 421 and 422 may be in contact with the skin of the user. Accordingly, it is not possible to effectively provide the current set to the skin of the user. In addition, when the second height h2 is less than about 75% of the first height h1, a phenomenon that cosmetics or drugs disposed between the head part 2000 and the skin of the user move to an edge region of the head part 2000 or move to a central region of the head part 2000, may occur.

In addition, when the second height h2 exceeds 95% of the first height h1, the first to fourth contact portions 411, 412, 421, and 422 may not be effectively in contact with the flexed skin region of the user.

Therefore, it is desirable to satisfy the range of the heights h1 and h2 of the first to fourth contact portions 411, 412, 421, and 422 described above in order to be effectively in contact with a flat or relatively flexed skin region, and to prevent the cosmetics or drugs from moving to the outside or the center of the skin care device 1.

The second electrode part 420 may include a curved surface. For example, an upper surface of the second electrode part 420 facing the skin of the user may include a curved surface. Specifically, the third contact portion 421 and the fourth contact portion 422 in contact with the skin of the user may include a curved surface. More specifically, the third contact surface 421S and the fourth contact surface 422S may include a curved surface. The third contact surface 421S and the fourth contact surface 422S may be curved surfaces that are convex in a direction of the skin of the user. At this time, the third contact surface 421S and the fourth contact surface 422S may be curved surfaces having the same curvature radius.

For example, the curvature radius of the third contact surface 421S and the fourth contact surface 422S may be about 100 mm to about 200 mm. Specifically, the curvature radius of the third contact surface 421S and the fourth contact surface 422S may be about 120 mm to about 180 mm. When the curvature radius of the third contact surface 421S and the fourth contact surface 422S is less than about 100 mm, surfaces of the third and fourth contact portions 421 and 422 have a relatively large curvature R value, and thus a massage effect may be increased, but it is difficult to effectively provide current to the skin of the user. In addition, when the curvature radius of the third contact surface 421S and the fourth contact surface 422S exceeds about 200 mm, an effect of being able to massage the skin is reduced by a relatively small curvature value. Therefore, it is desirable to satisfy the range of the third contact surface 421S and the fourth contact surface 422S described above in consideration of effectively providing the current to the skin of the user, and simultaneously, of the massage effect by the third and fourth contact portions 421 and 422.

The curvature radius of the third contact surface 421S and the fourth contact surface 422S may be greater than or equal to the curvature radius of the first contact surface 411S and the second contact surface 412S.

As an example, the curvature radius of the third and fourth contact surfaces 421S and 422S may be provided in the same as the curvature radius of the first and second contact surfaces 411S and 412S. Accordingly, when the skin of the user is rolled by the skin care device 1, the skin of the user may be massaged while uniformly providing the set current.

As still another example, the curvature radius of the third and fourth contact surfaces 421S and 422S may be provided larger than that of the first and second contact surfaces 411S and 412S. Accordingly, when the skin care device 1 is rolled on the skin of the user, a skin massage function may be maximized. In addition, it is possible to minimize the movement of cosmetics or drugs located between the head part 2000 and the skin of the user to the edge or central region of the head part 2000.

That is, in the embodiment, the contact characteristics of the flexed skin of the user and the first to fourth contact portions 411, 412, 421, and 422 may be maximized by the contact surfaces 411S, 412S, 421S, and 422S having the set curvature radius, and it is possible to minimize the movement of the cosmetics or drugs between the first and second electrode parts 410 and 420 to the edge or central region of the head part 2000.

The second electrode part 420 may further include a third connecting portion 423 and a fourth connecting portion 424. The third connecting portion 423 and the fourth connecting portion 424 may be disposed at both ends of the second contact portion 412 and the fourth contact portion 422 respectively to connect the third contact portion 421 and the fourth contact portion 422.

The third connecting portion 423 and the fourth connecting portion 424 may have shapes corresponding to each other. As an example, the third connecting portion 423 and the fourth connecting portion 424 may be spaced apart from each other while facing each other in the second direction (y-axis direction). In addition, the third connecting portion 423 and the fourth connecting portion 424 may be symmetrical with respect to a virtual line in the first direction (x-axis direction).

The third connecting portion 423 and the fourth connecting portion 424 may not be exposed to the outside of the skin care device 1. For example, the third connecting portion 423 and the fourth connecting portion 424 may have a form that is bent and extended in the direction of the substrate 200 from the both ends of each of the third contact portion 421 and the fourth contact portion 422. Specifically, the third connecting portion 423 and the fourth connecting portion 424 may have a lower height than the third contact portion 421 and the fourth contact portion 422. Upper surfaces of the third connecting portion 423 and the fourth connecting portion 424 may be disposed below the upper surface 501 of the cover part 500. The third connecting portion 423 and the fourth connecting portion 424 may be provided in a concave shape at both ends of each of the third contact portion 421 and the fourth contact portion 422.

The third and fourth connecting portions 423 and 424 provide a space in which the cover part 500 may be disposed, and may be disposed below the cover part 500. Specifically, the cover part 500 may be disposed on the third and fourth connecting portions 423 and 424, which are a space between the third and fourth contact portions 421 and 422, and thus it is possible to have improved reliability in a central region of the head part 2000. In addition, the cover part 500 is disposed on the first and second connecting portions 413 and 414, and accordingly, the second electrode part 420 may be effectively supported. For example, a fixing protrusion (not shown) extending in an upper surface direction of the third and fourth connecting portions 423 and 424 may be formed on a lower surface of the cover part 500. A fixing groove (not shown) corresponding to the fixing protrusion may be formed on the upper surface of each of the third and fourth connecting portions 423 and 424. Accordingly, when the cover part 500 is connected to the housing 100, the fixing protrusion of the cover part 500 may be disposed to be inserted into the fixing groove, and accordingly, the second electrode part 420 may be fixedly disposed at a set position.

In addition, the embodiment may include a second terminal portion 425 that connects the second electrode part 420 and the substrate 200. The second terminal portion 425 may be extended in the direction of the substrate 200 from at least one configuration of the third contact portion 421, the fourth contact portion 422, the third connecting portion 423, and the fourth connecting portion 424. As an example, the second terminal portion 425 may be connected to the fourth contact portion 422, and may be extended in the direction of the substrate 200 from a lower surface of the fourth contact portion 422. The second terminal portion 425 may be in direct contact with the substrate 200, and may be electrically connected to the substrate 200, and the set current may be applied to the second electrode part 420 via the second terminal portion 425.

As described above, the first electrode part 410 and the second electrode part 420 according to the embodiment may include a curved surface. Specifically, the first to fourth contact surfaces 411S, 412S, 421S, and 422S may include curved surfaces.

However, the embodiment is not limited thereto, and the first to fourth contact surfaces 411S, 412S, 421S, and 422S facing and contacting the skin may be provided in a plane. In this case, the first to fourth contact surfaces 411S, 412S, 421S, and 422S may have an inclined shape with respect to a virtual line connecting the lower surfaces of the first and second electrode parts 410 and 420.

For example, a height of each of the first to fourth contact portions 411, 412, 421, and 422 may be changed. Specifically, the heights of the first to fourth contact portions 411, 412, 421, and 422 may be changed from a center of the substrate 200 toward an edge of the substrate 200. More specifically, the height of each of the first and second contact portions 411 and 412 may be reduced from an inner circumferential surface of the first electrode part 410 toward an outer circumferential surface. The height of each of the third and fourth contact portions 421, 422 may be reduced from an inner circumferential surface of the second electrode part 420 toward an outer circumferential surface.

In addition, the first electrode part 410 may include the above-mentioned first height h1 defined by a height to the uppermost portion from the lower surface thereof, and the second electrode part 420 may include the above-mentioned second height h2 defined by a height to the uppermost portion from the lower surface thereof. In this case, the first height h1 which is the maximum height of the first electrode part 410, may be higher than the second height h2 which is the maximum height of the second electrode part 420.

Accordingly, the first to fourth contact surfaces 411S, 412S, 421S, and 422S may have an inclined shape, and thus contact characteristics with the skin may be improved. Therefore, it is possible to effectively contact the skin of the flexed region such as a chin and cheekbones of the user, and thus it is possible to be maximize the massage effect.

Referring to FIG. 7, a cover part 500 according to an embodiment may include a plurality of holes. Specifically, the cover part 500 may include a plurality of holes corresponding to the electrode part 400. For example, the cover part 500 may include a first hole 511 and a second hole 512 formed in regions corresponding to the first and second contact portions 411 and 412, respectively. Specifically, each of the first and second holes 511 and 512 may be disposed in a region vertically overlapped with the first and second contact portions 411 and 412, and may have a shape corresponding to each of the first and second contact portions 411 and 412. A part of the first electrode part 410, for example, a part of the first contact portion 411 may be disposed to be inserted into the first hole 511, and a part of the first electrode part 410, for example, a part of the second contact portion 412 may be disposed to be inserted into the second hole 512.

At this time, a partial region of each of the first and second contact portions 411 and 412 may be disposed at a lower portion of the cover part 500, and a remaining region of each of the first and second contact portions 411 and 412 may protrude from the upper surface 501 of the cover part 500. That is, the first and second contact surfaces 411S and 412S may be disposed above the upper surface 501 of the cover part 500, and may be in contact with the skin of the user.

At this time, a partial region of each of the third and fourth contact portions 421 and 422 may be disposed at the lower portion of the cover part 500, and a remaining region of each of the third and fourth contact portions 421 and 422 may protrude from the upper surface 501 of the cover part 500. That is, the third and fourth contact surfaces 421S and 422S may be disposed above the upper surface 501 of the cover part 500, and may be in contact with the skin of the user together with the first and second contact surfaces 411S and 412S.

The cover part 500 may include a support portion. At least one of the support portions may be disposed on a lower region of the cover part 500, and may control positions of the first electrode part 410 and the second electrode part 420.

As an example, the cover part 500 may include a plurality of support portions that support the first and second electrode parts 410 and 420. Specifically, the plurality of support portions may include a first support portion 521 and a second support portion 522 that extend in one direction, and may include a third support portion 523 that extends in another direction different from the one direction. For example, the first support portion 521 and the second support portion 522 may extend in the second direction (y-axis direction), and the third support portion 523 may extend in in the first direction (x-axis direction).

More specifically, as shown in FIG. 7, when viewing the cover part 500 in a plane, the first support portion 521 may extend upward from a center of the cover part 500. The second support portion 522 may extend downward from the center of the cover part 500. In addition, the third support portion 523 may extend in a direction perpendicular to the first support portion 521 and the second support portion 522.

The first support portion 521 may support the first electrode part 410 and the second electrode part 420. For example, the first support portion 521 may be disposed in a region corresponding to one end of the first contact portion 411, one end of the second contact portion 412, one end of the third contact portion 421, and one end of the fourth contact portion 422 to support the ends, respectively. In addition, the first support portion 521 may be disposed in a region corresponding to a first connecting portion 413 connecting between the first contact portion 411 and the second contact portion 412, and the third connecting portion 423 connecting between the third contact portion 421 and the fourth contact portion 422 to support the first and third connecting portions 413 and 423.

The second support portion 522 may support the first electrode part 410 and the second electrode part 420. For example, the second support portion 522 may be disposed in a region corresponding to the other end of the first contact portion 411, the other end of the second contact portion 412, the other end of the third contact portion 421, and the other end of the fourth contact portion 422 to support the ends, respectively. In addition, the second support portion 522 may be disposed in a region corresponding to a second connecting portion 414 connecting between the first contact portion 411 and the second contact portion 412, and a fourth connecting portion 424 connecting between the third contact portion 421 and the fourth contact portion 422 to support the second and fourth connecting portions 414 and 424.

The third support portion 523 may support the first electrode part 410 and the second electrode part 420. For example, the third support portion 523 may be disposed in a region corresponding to a central region of the first contact portion 411 and the third contact portion 421 to support the central regions of the contact portions. In addition, the third support portion 523 may be disposed in a region corresponding to a central region of the second contact portion 412 and the fourth contact portion 422 to support the central regions of the contact portions.

The first and second electrode parts 410 and 420 may be effectively supported by the first to third support portions 521, 522, and 523. As an example, when the head part 2000 is in contact with the skin of the user, positions of the first and second electrode parts 410 and 420 may be changed by contact pressure. Specifically, at least one of the first to fourth contact portions 411, 412, 421, and 422 may be moved downward from the upper surface 501 of the cover part 500 by the contact pressure. Accordingly, contact characteristics between the contact portions 411, 412, 421, and 422 and the skin are deteriorated, and thus the set current may not be provided to the skin of the user.

However, the first to fourth contact portions 411, 412, 421, and 422 according to the embodiment may be disposed at positions set by the first to third support portions 521, 522, and 523. That is, the first to fourth contact portions 411, 412, 421, and 422 may be disposed protruding upward from the upper surface 501 of the cover part 500 even though the contact pressure is applied, and accordingly, it possible to effectively provide the set current to the skin of the user.

Figure 8:
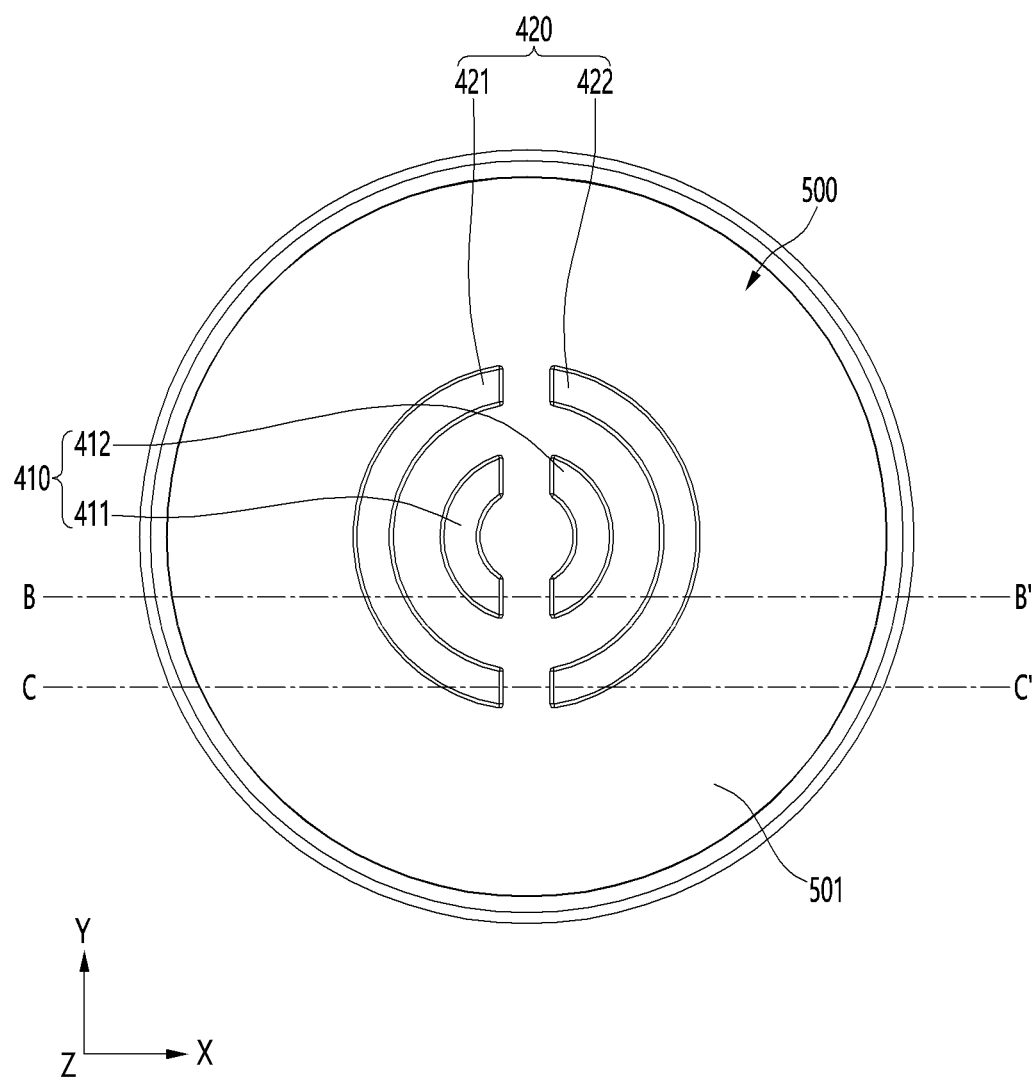
FIG. 8 is a top view of a head part according to an embodiment.
Figure 9:
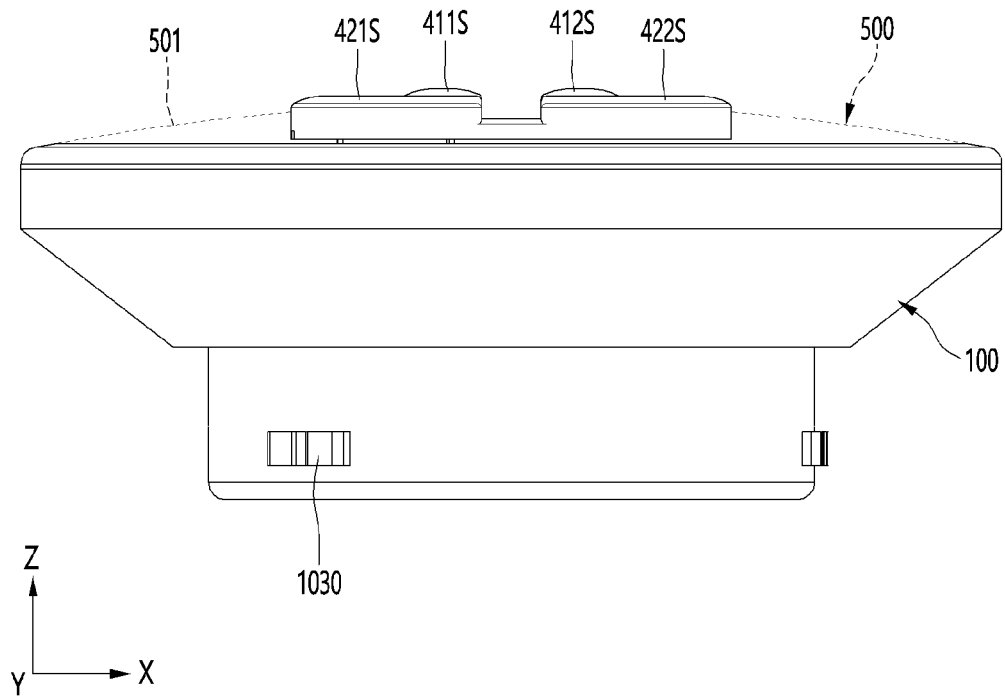
FIG. 9 is a side view of the head part according to the embodiment.
Figure 10:
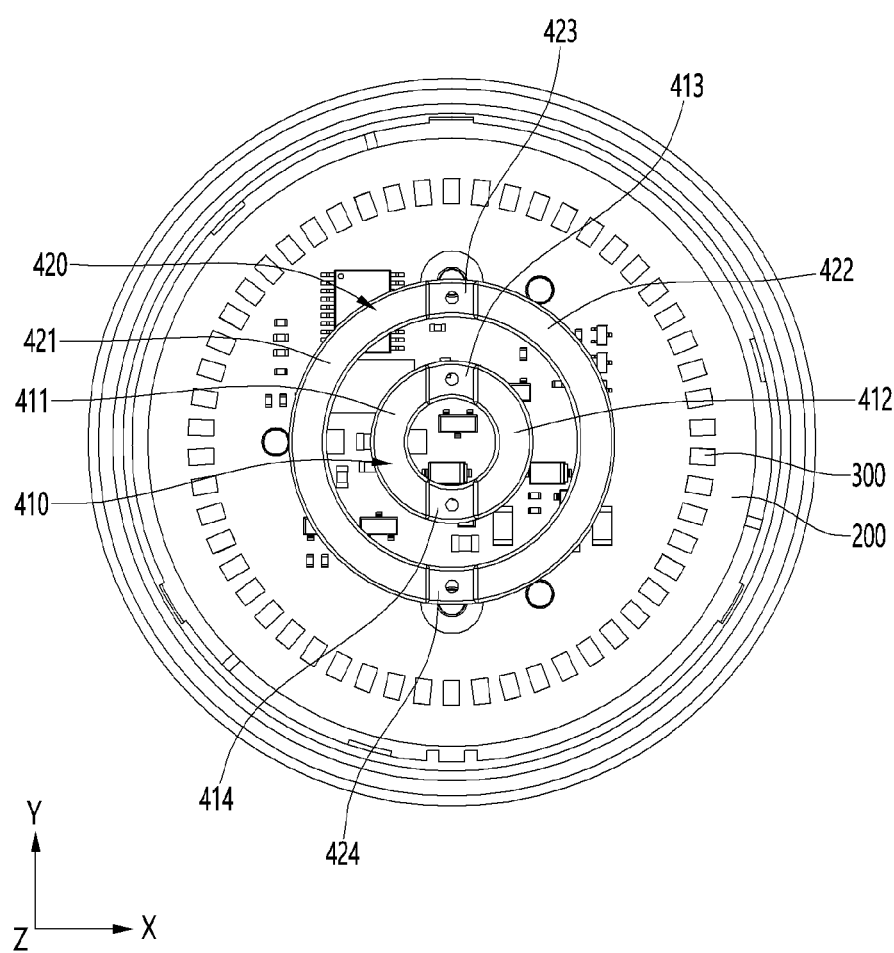
FIG. 10 is a top view in which a cover part is removed from the head part according to the embodiment.
Figure 11:
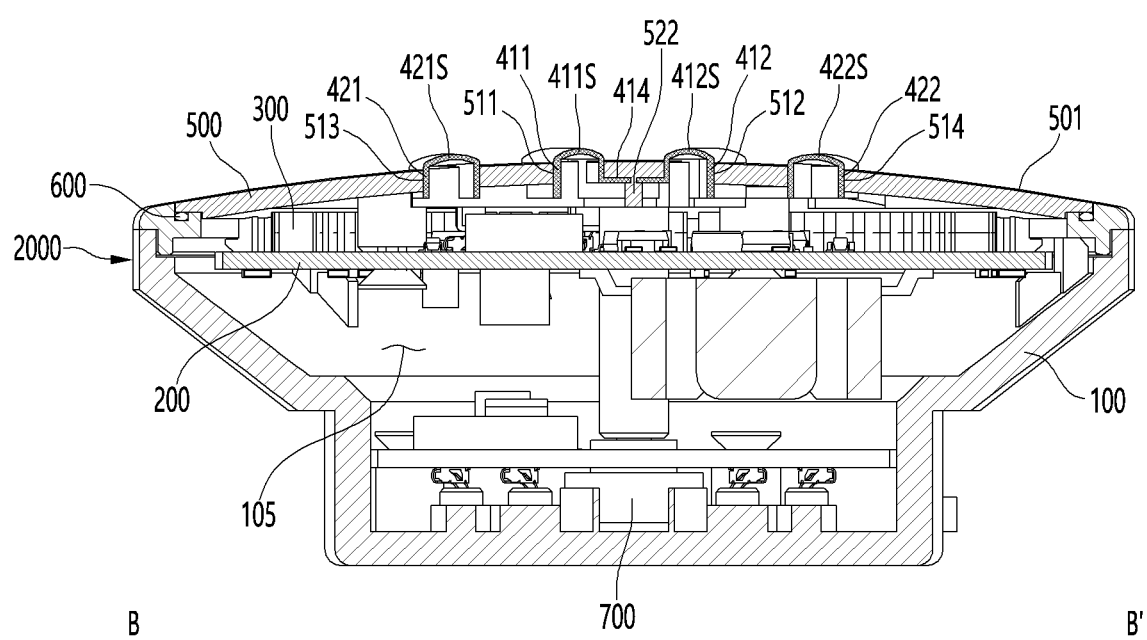
FIG. 11 is a cross-sectional view showing a cross section taken along line B-B' of FIG. 8.
Figure 12:
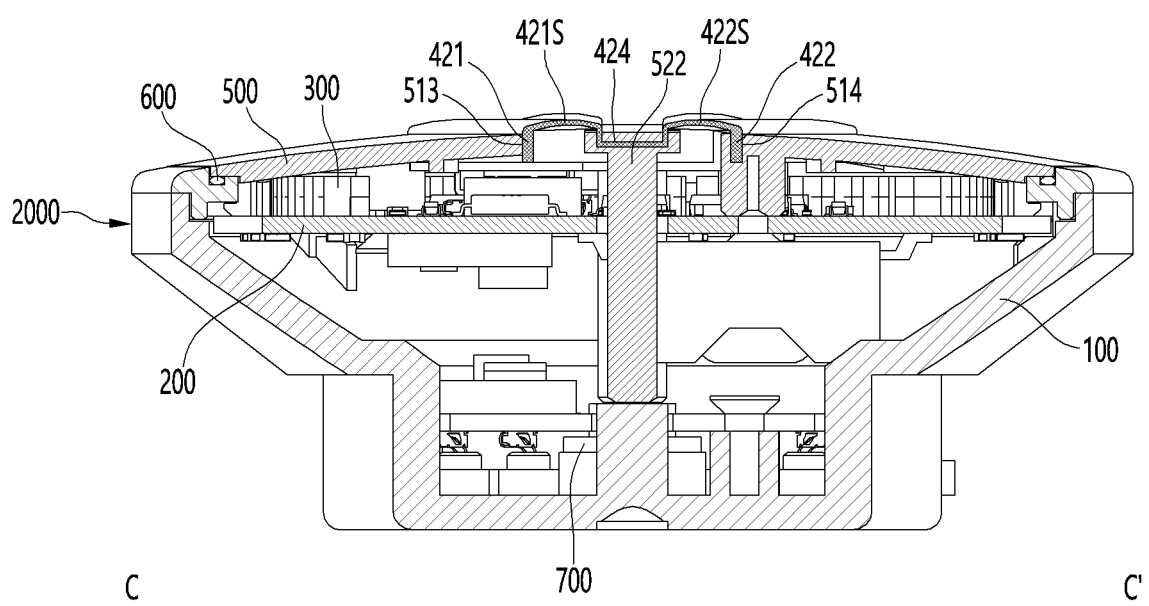
FIG. 12 is a cross-sectional view showing a cross section taken along line C-C' of FIG. 8.
Figure 12:
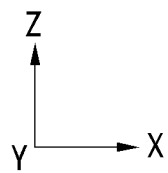

FIG. 8 is a top view of a head part according to an embodiment, and FIG. 9 is a side view of the head part according to the embodiment. In addition, FIG. 10 is a top view in which a cover part is removed from the head part according to the embodiment. FIGS. 11 and 12 are views showing a cross section taken along line B-B' and a cross section taken along line C-C' of FIG. 8, respectively.

Referring to FIGS. 8 and 9, a part of the first electrode part 410 and the second electrode part 420 may be exposed on the upper surface 501 of the cover part 500. Specifically, the first contact portion 411, the second contact portion 412, the third contact portion 421, and the fourth contact portion 422 may be disposed in a region overlapped with a hole formed in the cover part 500 to be exposed. On the other hand, the first connecting portion 413, the second connecting portion 414, the third connecting portion 423, and the fourth connecting portion 424 may be formed in a region not overlapped with the hole formed in the cover part 500 to be disposed in a lower portion of the cover part 500, for example, in the housing 100. Accordingly, the first to fourth connecting portions 413, 414, 423, and 424 may not be exposed to the outside by the cover part 500.

The first and second electrode parts 410 and 420 may be disposed at positions set by the plurality of support portions 521, 522, and 523 described above, and the contact surfaces 411S, 412S, 421S, and 422S of each of the first to fourth contact portions 411, 412, 421, and 422 may be disposed so as to protrude by a predetermined height from the upper surface 501 of the cover part 500. Accordingly, when the user uses the skin care device 1 to care for the skin, the first to fourth contact portions 411, 412, 421, and 422 may effectively provide a set current in close contact with the skin of the user without being spaced apart from the skin, and the contact surfaces 411S, 412S, 421S, and 422S may include curved surfaces to massage the skin effectively.

In addition, the upper surface 501 of the cover part 500 may be a curved surface. For example, the upper surface 501 of the cover part 500 may be a curved surface that is convex toward the skin of the user. Specifically, a curvature radius of the upper surface 501 of the cover part 500 may be about 100 mm to about 200 mm. More specifically, the curvature radius of the upper surface 501 of the cover part 500 may be from about 120 mm to about 180 mm.

When the curvature radius of the upper surface 501 of the cover part 500 is less than about 100 mm, the upper surface 501 of the cover part 500 has a relatively large curvature R value, and thus adhesion characteristics with the skin of the user may be deteriorated. Accordingly, an effect that the skin of the user may be massaged by the surface of the head part 2000 may be lowered. In addition, when the curvature radius of the upper surface 501 of the cover part 500 exceeds about 200 mm, contact characteristics with the skin of the user may be deteriorated by a relatively small curvature value. For example, the contact characteristics between a flexed skin region of the user and the head part 2000 may be deteriorated by the curvature value, and thus the massage effect may be lowered.

The upper surface 501 of the cover part 500 may have the same curvature radius as at least one of the first to fourth contact surfaces 411S, 412S, 421S, and 422S. For example, the upper surface 501 of the cover part 500 may have the same curvature radius as the first and second contact surfaces 411S and 412S. As another example, the upper surface 501 of the cover part 500 may have the same curvature radius as the third and fourth contact surfaces 421S and 422S. As still another example, when the first to fourth contact surfaces 411S, 412S, 421S, and 422S have the same curvature radius, the upper surface 501 of the cover part 500 may be provided with the same curvature radius as the first to fourth contact surfaces 411S, 412S, 421S, and 422S. Accordingly, a uniform electric current may be supplied to the skin of the user, and at the same time, the skin may be effectively massaged through the cover part 500 and the electrode parts 410 and 420.

Referring to FIGS. 10 to 12, a plurality of light emitting elements 300, a first electrode part 410, and a second electrode part 420 may be disposed on the substrate 200. The plurality of light emitting elements 300, the first electrode part 410, and the second electrode part 420 may be electrically connected to the substrate 200, and may operate based on a signal applied from a control unit (not shown).

First, the plurality of light emitting elements 300 may emit light in a wavelength band set toward the skin of the user. The plurality of light emitting elements 300 may be disposed in a region not overlapped with the first and second electrode parts 410 and 420 in a vertical direction (z-axis direction). Specifically, the plurality of light emitting elements 300 may be disposed around the second electrode part 420, and may be disposed along a concentric circumference from a center of the substrate 200. Accordingly, it is possible to prevent or minimize the loss of light emitted from the plurality of light emitting elements 300 by the first and second electrode parts 410 and 420, and the light may be effectively emitted to the outside of the head part 2000.

The plurality of light emitting elements 300 may emit light in a visible light band. For example, the plurality of light emitting elements 300 may emit visible light of at least one color of red, orange, and green.

For example, the plurality of light emitting elements 300 may include a first light emitting element that emits red light. The first light emitting element may emit red light toward the outside of the head part 2000, for example, toward the skin of the user. At this time, the red light of the first light emitting element may penetrate into a dermis tissue of the skin, and may assist generation of collagen, and accordingly, it is possible to improve regeneration and elasticity characteristics of the skin. In addition, the red light of the first light emitting element may activate sebaceous glands in a deep site of the skin, and may be useful for treating inflammation and wounds.

In addition, the plurality of light emitting elements 300 may include a second light emitting element that emits orange light. The second light emitting element may emit orange light toward the outside of the head part 2000, for example, toward the skin of the user. At this time, the orange light of the second light emitting element may suppress generation of melanin, may improve spots, freckles, etc., and may smooth blood circulation. In addition, the orange light of the second light emitting element may reduce inflammation that induces red spots and wrinkles.

In addition, the plurality of light emitting elements 300 may include a third light emitting element that emits green light. The third light emitting element may emit green light toward the outside of the head part 2000, for example, toward the skin of the user. At this time, the green light of the third light emitting element may be effective in improving fine wrinkles formed on the skin, and may help metabolism of the skin to revitalize. In addition, the green light of the third light emitting element may provide a soothing effect on the skin.

The first to third light emitting elements may be disposed in the same number on the substrate 200. In addition, the first to third light emitting elements may be disposed according to a rule set on the substrate 200. For example, the first to third light emitting elements may be disposed on the substrate 200 in the order of the first light emitting element, the second light emitting element, and the third light emitting element along the concentric circumference in one cycle.

The plurality of light emitting elements 300 may provide at least one of red, orange, and green light to the skin of the user by the control of the user. Accordingly, the skin care device 1 may selectively provide various effects according to the color of visible light to the skin of the user. However, the embodiment is not limited thereto, and the plurality of light emitting elements 300 may provide light of various colors to the skin of the user. As an example, the light emitting element 300 may provide blue light to the skin of the user to sterilize the skin of the user.

The skin care device 1 according to the embodiment may provide at least one of a high frequency current, a microcurrent, and a galvanic current to the skin of the user.

As an example, the high frequency current may flow to the first electrode part 410 and the second electrode part 420. Specifically, currents having different polarities may flow to the first electrode part 410 and the second electrode part 420. Accordingly, current having the same polarity flows to the first contact portion 411 and the second contact portion 412, and current having a polarity different from that of the first and second contact portions 411 and 412 may flow to the third contact portion 421 and the fourth contact portion 422.

Accordingly, the high-frequency current may flow between the first contact portion 411 and the third contact portion 421, and may flow between the second contact portion 412 and the fourth contact portion 422, through the skin of the user. Therefore, a deep heat generation zone may be formed by the high frequency current in each of a region between the first contact portion 411 and the third contact portion 421 and a region between the second contact portion 412 and the fourth contact portion 422. A temperature of a skin tissue may be raised by the deep heat. For example, the temperature of the skin tissue may be raised to about 40° C. or more by the deep heat. At this time, when the temperature of the skin tissue is raised by the deep heat, dilation of arteries and capillaries may occur, and a blood flow may be increased, and thus there is an effect that blood circulation and metabolism are promoted. In addition, the deep heat may promote generation of collagen and has an effect of decomposing cellulite. Accordingly, the user may obtain an effect of lifting the skin.

In addition, the microcurrent may flow to the first electrode part 410 and the second electrode part 420. That is, the microcurrent may flow to the first to fourth contact portions 411, 412, 421, and 422 in contact with the skin of the user, and the microcurrent may be provided to the skin in contact with the contact portions 411, 412, 421, and 422. For example, the first electrode part 410 and the second electrode part 420 may provide a microcurrent having a shape similar to a bioelectric current of the user. Specifically, the first to fourth contact portions 411, 412, 421, and 422 may provide a microcurrent of less than about 1000 µA to the skin of the user.

Accordingly, the microcurrent provided to the skin of the user may increase a generation amount of adenosine triphosphate (ATP), which is a basic energy source of physical activity, and improve the permeability of cell membranes to accelerate discharge of wastes. In addition, it may also synthesize collagen and elastin in the skin to help solve aging problems such as skin moisture, elasticity and wrinkles.

In addition, the galvanic current may flow to the first electrode part 410 and the second electrode part 420. For example, a set current may be applied to the first electrode part 410 and the second electrode part 420 to provide an iontophoresis method. Specifically, current having the same polarity may flow to the first electrode part 410 and the second electrode part 420. That is, the current having the same polarity may flow to the first to fourth contact portions 411, 412, 421, and 422.

The first to fourth contact portions 411, 412, 421, and 422 may form a potential difference in the skin to change an electrical environment of the skin. As an example, the first to fourth contact portions 411, 412, 421, and 422 may be conductive to a positive polarity (+). In this case, the contact portions 411, 412, 421, and 422 may effectively discharge the wastes inside the skin. Specifically, the contact portions 411, 412, 421, and 422 may effectively discharge anion (−) waste products located inside the skin by an electric attraction. In addition, the first to fourth contact portions 411, 412, 421, and 422 may be conductive to a negative polarity (−). In this case, a cosmetic or drug disposed between the contact portions 411, 412, 421, and 422 and the skin of the user may be effectively provided to the skin. Specifically, the contact portions 411, 412, 421, and 422 may effectively permeate anions (−) contained in cosmetics and drugs into the skin by electric repulsive force.

That is, the first electrode part 410 and the second electrode part 420 according to the embodiment apply the current on the skin side to effectively provide to the skin ionic cosmetics, drugs, and ionic active ingredients applied to the skin, and to effectively discharge the wastes.

The skin care device 1 according to the embodiment may provide vibration to the skin of the user. Specifically, the skin care device 1 may include a vibrating member 700 disposed in the head part 2000. The vibrating member 700 may be disposed on a lower surface of the accommodation space 105. The vibrating member 700 may be disposed in a region corresponding to a central region of the lower surface of the accommodation space 105, or may be disposed in a region adjacent to the central region. Accordingly, the vibrating member 700 may provide vibration of uniform strength to a surface of the head part 2000 and the skin of the user in contact with the surface.

The vibration generated by the vibrating member 700 may massage a region of the skin in contact with the head part 2000. For example, the vibration generated by the vibrating member 700 may smooth blood circulation, and may provide elasticity to the skin. In addition, the vibration of the vibrating member 700 may separate contaminants disposed on the surface of the skin or wastes in pores from the skin. In addition, the vibration generated by the vibrating member 700 may cause cracks in a corneum formed on the surface of the skin or expand a gap between the corneums to provide a movement path of cosmetics or drugs. Accordingly, the skin care device 1 may be used to effectively supply cosmetics or drugs inside the skin.

The skin care device 1 according to the embodiment may be operated in various modes by a control of the user. As an example, the skin care device 1 may provide at least one of visible light, current, and vibration by the control of the user.

As an example, the skin care device 1 may operate only a plurality of light emitting elements 300 by the control of the user, and the electrode parts 410 and 420 and the vibrating member 700 may not be operated. Accordingly, the skin care device 1 may provide visible light of at least one color of red, orange, and green to the skin of the user.

In addition, the skin care device 1 may operate only the plurality of light emitting elements 300 and the electrode parts 410 and 420 by the control of the user, and the vibrating member 700 may not be operated. Accordingly, the skin care device 1 may provide visible light, and simultaneously at least one selected from a high frequency current, a galvanic current, and a microcurrent to the skin of the user.

In addition, in the skin care device 1, the plurality of light emitting elements 300, the electrode parts 410 and 420, and the vibrating member 700 may operate simultaneously by the control of the user. Accordingly, the skin care device 1 may provide visible light and vibration to the skin of the user and simultaneously, selectively provide current to effectively beautify or treat the skin of the user. That is, the skin care device 1 according to the embodiment may provide at least one of visible light, current, and vibration to the skin of the user to effectively beautify or treat the skin of the user.

In addition, in the skin care device 1 according to the embodiment, the head part 2000 may be provided so as to be detachable from the main body 1000. Accordingly, when the main body 1000 or the head part 2000 is damaged or malfunctions, only a damaged region may be repaired or replaced. In addition, when the user uses another function different from the above-mentioned functions, the head part including the other function may be used by connecting to the main body 1000 without purchasing or providing a new skin care device having the other function.

The characteristics, structures and effects described in the embodiments above are included in at least one embodiment but are not limited to one embodiment. Furthermore, the characteristics, structures, effects, and the like illustrated in each of the embodiments may be combined or modified even with respect to other embodiments by those of ordinary skill in the art to which the embodiments pertain. Thus, it would be construed that contents related to such a combination and such a modification are included in the scope of the embodiments.

In addition, embodiments have been mostly described above, but they are only examples and do not limit the present invention, and a person skilled in the art to which the present invention pertains may appreciate that several variations and applications not presented above may be made without departing from the essential characteristics of the embodiments. For example, each of components described in detail in the embodiment may be modified to implement. In addition, it should be construed that differences related to such variations and applications are included in the scope of the present invention defined in the appended claims.

What is claimed is:

1. A skin care device, comprising:
a main body; and
a head part connected to the main body,
wherein the head part includes:
a housing in which an upper portion thereof is open, and including an accommodation space therein;

a first electrode part and a second electrode part disposed in the housing;
a plurality of light emitting elements disposed in the housing and spaced apart from the first electrode part and the second electrode part; and
a cover part for shielding of the open upper region of the housing,
wherein the cover part includes a plurality of through holes formed in a region corresponding to the first electrode part and the second electrode part, a part of each of the first electrode part and the second electrode part protrudes from an upper surface of the cover part via the plurality of through holes, and an upper surface of each of the first electrode part and the second electrode part exposed to an outside includes a convex curved surface toward the outside,
wherein the second electrode part surrounds a periphery of the first electrode part,
wherein the first electrode part includes:
a first contact portion and a second contact portion; and
a first connecting portion and a second connecting portion between the first and second contact portions, wherein each of the first and second connecting portions has a lower height than each of the first and second contact portions such that a pair of recesses are formed between the first contact portion and the second contact portion,
wherein the second electrode part includes:
a third contact portion and a fourth contact portion; and
a third connecting portion and a fourth connecting portion between the third and fourth contact portions, wherein each of the third and fourth connecting portions has a lower height than the third and fourth contact portions such that a pair of recesses are formed between the third contact portion and the fourth contact portion,
wherein each of the first and second contact portions of the first electrode and each of the third and fourth contact portions of the second electrode are overlapped with a respective through hole of the plurality of through holes of the cover part to be exposed to the outside, and
wherein each of the first and second connecting portions of the first electrode and each of the third and fourth connecting portions of the second electrode are covered with a respective support portion of a plurality of support portions of the cover between the respective through holes of the plurality of through holes of the cover part to be covered from the outside.

2. The skin care device of claim 1, wherein the first and second electrode parts have an annular planar shape and are spaced apart from each other,
the second electrode part is disposed at equal distances with the first electrode part,
the first electrode part has a first diameter defined as a diameter of an outer circumferential surface of the first electrode part,
the second electrode part has a second diameter defined as a diameter of an inner circumferential surface of the second electrode part, and
the second diameter is larger than the first diameter.

3. The skin care device of claim 2, wherein the first and second contact portions are exposed to the outside of the skin care device, face each other in a first direction, and are spaced apart from each other,
the third and fourth contact portions are exposed to the outside of the skin care device, face each other in the first direction, and are spaced apart from each other,
the first to fourth contact portions are disposed in a region overlapped with the plurality of through holes of the cover part in a vertical direction,
each of the first to fourth contact portions includes first to fourth contact surfaces defined as an upper surface exposed to the outside, respectively, and
the first to fourth contact surfaces including a convex curved surface are disposed higher than the upper surface of the cover part.

4. The skin care device of claim 3, wherein a radius of curvature of the first to fourth contact surfaces is the same.

5. The skin care device of claim 3, wherein the upper surface of the cover part has the same radius of curvature as at least one of the first to fourth contact surfaces.

6. The skin care device of claim 3, wherein a maximum height of the second electrode part is lower than that of the first electrode part.

7. The skin care device of claim 6, wherein the maximum height of the second electrode part is 75% to 95% of the maximum height of the first electrode part.

8. The skin care device of claim 3, wherein the first and second connecting portions connect both ends of the first and second contact portions, respectively,
the third and fourth connecting portions connect both ends of the third and fourth contact portions, respectively,
the first and second connecting portions face each other in a second direction different from the first direction and are spaced apart from each other,
the third and fourth connecting portions face each other in the second direction and are spaced apart from each other, and
the first to fourth connecting portions are disposed in the housing not overlapped with the plurality of through holes in the vertical direction.

9. The skin care device of claim 8, wherein a fixing groove is formed on an upper surface of the first and second connecting portions,
a fixing protrusion extending in an upper surface direction of the first and second connecting portions is formed on a lower surface of the cover part, and
the fixing protrusion is disposed in a region corresponding to the fixing groove.

10. The skin care device of claim 8, wherein the support portions include a first support portion disposed in a region corresponding to the first and third connecting portions, and a second support portion disposed in a region corresponding to the second and fourth connecting portions.

11. The skin care device of claim 3, wherein a radius of curvature of the third and fourth contact surfaces is larger than that of the first and second contact surfaces.

12. The skin care device of claim 3, wherein currents of the same polarity or opposite polarities flow to the first and second electrode parts.

13. The skin care device of claim 2, wherein a cross-sectional shape of each of the first and second electrode parts has a U-shape that is turned upside down in an opposite direction.

14. The skin care device of claim 2, wherein a lower surface of each of the first and second electrode parts is disposed to face a substrate,
a recess is formed on the lower surface of each of the first and second electrode parts, the recess on the lower surface of the first electrode part has a concave shape toward an upper surface from the lower surface of the first electrode part, and the recess on the lower surface of the second electrode part has a concave shape toward an upper surface from the lower surface of the second electrode part.

15. The skin care device of claim 1, wherein the first electrode part and the second electrode part provide at least one of a galvanic current, a high frequency current, or a microcurrent.

16. The skin care device of claim 1, comprising
a vibration member disposed in the housing,
wherein the vibration member generates low-frequency or medium-frequency energy toward the upper surface of the cover part.

17. The skin care device of claim 1, wherein the plurality of light emitting elements are disposed around the first electrode part and the second electrode part and emit light in at least one wavelength band of red wavelength band, green wavelength band, and orange wavelength band.

18. The skin care device of claim 17, wherein the cover part is translucent or opaque, and includes a material through which light emitted from the plurality of light emitting elements is transmitted.

19. The skin care device of claim 1, comprising
a sealing member disposed between the housing and the cover part.

20. The skin care device of claim 1, wherein the head part is detachable from the main body.

\* \* \* \* \*